(12) United States Patent
Johansson et al.

(10) Patent No.: US 6,533,767 B2
(45) Date of Patent: *Mar. 18, 2003

(54) METHODS FOR ENHANCING FLUID FLOW THROUGH AN OBSTRUCTED VASCULAR SITE, AND SYSTEMS AND KITS FOR USE IN PRACTICING THE SAME

(75) Inventors: Peter Johansson, Campbell, CA (US); David Delaney, Los Gatos, CA (US); Brent Constantz, Menlo Park, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/774,469

(22) Filed: Jan. 30, 2001

(65) Prior Publication Data

US 2001/0039411 A1 Nov. 8, 2001

Related U.S. Application Data

(63) Continuation-in-part of application No. 09/528,576, filed on Mar. 20, 2000.

(51) Int. Cl.$^7$ .............................................. A61M 31/00
(52) U.S. Cl. ........................ 604/507; 604/508; 604/509; 604/264; 604/96.01; 604/912
(58) Field of Search ........................... 604/164.09, 173, 604/101.01, 101.02, 101.03, 101.04, 101.05, 102.01, 102.03, 96.01, 507, 508, 509, 264, 183, 912; 606/192, 193, 194, 198, 159

(56) References Cited

U.S. PATENT DOCUMENTS

| | | |
|---|---|---|
| 3,993,080 A | 11/1976 | Loseff .......................... 128/350 |
| 4,329,994 A | 5/1982 | Cooper |
| 4,445,892 A | 5/1984 | Hussein et al. |
| 4,573,966 A | 3/1986 | Weikl et al. |
| 4,610,662 A | 9/1986 | Weikl et al. |
| 4,636,195 A | 1/1987 | Wolinsky |
| 4,655,746 A | 4/1987 | Daniels et al. |
| 4,690,672 A | 9/1987 | Veltrup |
| 4,824,436 A | 4/1989 | Wolinsky |
| 4,838,881 A | 6/1989 | Bennett |
| 4,911,163 A | 3/1990 | Fina |
| 4,976,733 A | 12/1990 | Girardot |
| 5,059,178 A | 10/1991 | Ya |
| 5,090,960 A | 2/1992 | Don Michael |
| 5,149,330 A | 9/1992 | Brightbill |
| 5,167,623 A | 12/1992 | Cianci et al. |
| 5,167,628 A | 12/1992 | Boyles |
| 5,195,955 A | 3/1993 | Don Michael |
| 5,207,648 A | 5/1993 | Gross |
| 5,222,941 A | 6/1993 | Don Michael |
| 5,370,609 A | 12/1994 | Drasler et al. |
| 5,372,131 A | 12/1994 | Heinen, Jr. ............. 128/207.15 |
| 5,380,284 A | 1/1995 | Don Michael |
| 5,443,446 A | 8/1995 | Shturman |
| 5,462,529 A | 10/1995 | Simpson et al. |
| 5,496,267 A | 3/1996 | Drasler et al. |
| 5,542,937 A | 8/1996 | Chee et al. |
| 5,785,675 A | 7/1998 | Drasler et al. |
| 5,833,650 A | 11/1998 | Imran |
| 6,013,068 A | 1/2000 | Spiegelhalter |
| 6,290,689 B1 * | 9/2001 | Delaney et al. ............. 604/264 |

OTHER PUBLICATIONS

Hargrove et al. (Dec. 1982), "Treatment of Acute Peripheral Arterial and Graft Thromboses with Low–Dose Streptokinase," *Surgery*, vol. 92(6):981–993.

Koltun et al. (Aug. 1987), "Thrombolysis in the Treatment of Peripheral Arterial Vascular Occlusions," *Arch Surg.*, vol. 122:901–905.

Olin et al. (Nov. 1998), "Thrombolytic Therapy in the Treatment of Peripheral Arterial Occlusions," *Annals of Emergency Medicine*, vol. 17:1210–1215.

Rickard et al. (Dec. 1997), "Limitations of Intra–Arterial Thrombolysis," *Cardiovascular Surgery*, vol. 5(6):634–640.

* cited by examiner

*Primary Examiner*—Manuel Mendez
*Assistant Examiner*—Mark Han
(74) *Attorney, Agent, or Firm*—Bret E. Field; Bozicevic, Field & Francis

(57) ABSTRACT

Methods of enhancing fluid flow through a vascular site occupied by a vascular occlusion, as well as systems and kits for use in practicing the same, are provided. In practicing the subject methods, the vascular site is flushed simultaneously with a first dissolution fluid (e.g., an organic matter dissolution fluid and/or an inorganic matter dissolution fluid), and a second dissolution fluid attenuating fluid, where flushing is carried out in a manner such that only a surface of the vascular occlusion is contacted with the non-attenuated dissolution fluid. Examples of dissolution fluid/dissolution fluid attenuating fluid pairs include: (1) oxidizing agent fluid and fluid comprising oxidizable neutralizing agent; (2) surfactant fluid and phosphate buffered saline; (3) acidic solution and phosphate buffered saline; etc. Flushing is carried out in this manner for a period of time sufficient for fluid flow through the vascular site to be enhanced, e.g. increased or established. The subject methods, systems and kits for practicing the same find use in the treatment of a variety of different vascular diseases characterized by the presence of vascular occlusions, including both partial and total occlusions.

24 Claims, 7 Drawing Sheets

METHODS FOR ENHANCING FLUID FLOW THROUGH AN OBSTRUCTED VASCULAR SITE, AND SYSTEMS AND KITS FOR USE IN PRACTICING THE SAME

CROSS-REFERENCE TO RELATED APPLICATIONS

This application is a continuation-in-part of application Ser. No. 09/528,576 filed Mar. 20, 2000, the disclosure of which is herein incorporated by reference.

INTRODUCTION

1. Technical Field

The field of this invention is vascular disease, particularly vascular diseases characterized by the presence of vascular occlusions, including both partial and total occlusions.

2. Background of the Invention

Vascular occlusions, which may be partial or total occlusions, play a prominent role in many types of vascular disease. Occlusions found in vascular disease may vary greatly in content, and are typically complex structures of two or more different types of components. Components found in vascular occlusions include: lipids; lipoproteins; proteins; including fibrinogen, collagen, elastin and the like; proteoglycans, such as chondroitin sulfate, heparin sulfate, dermatans, etc.; cells, including smooth muscle cells, epithelial cells, macrophages and lymphocytes; and minerals, e.g. calcium phosphates such as dahllite. An occlusion categorization system has been developed for use in characterizing vascular occlusions, where type IV, type V and type VI lesions, as defined in Stary et al., Arterioscler. Thromb. Vasc. Biol. (1995)15:1512–1531, are particularly relevant in vascular disease.

A variety of different protocols have been developed for use in treating vascular diseases characterized by the presence of partial or total occlusions. Such treatment methodologies generally involve mechanical removal or reduction of the size of the occlusion, and include: bypass surgery, balloon angioplasty, mechanical debridement, atherectomy, and the like.

Despite the plethora of different treatment strategies that have been developed for the treatment of vascular diseases associated with vascular occlusions, there are disadvantages associated with each technique, such as tissue damage, invasiveness, etc. For example, restenosis is a common complication that results in arteries in which occlusions have been mechanically removed.

As such, there is continued interest in the development of endovascular methods of treating vascular occlusions. Of particular interest would be the development of methods and devices suitable for use in the treatment of vascular occlusions which do not suffer from the disadvantages of currently employed devices and methods.

Relevant Literature

U.S. Pat Nos. of interest include: 4,445,892; 4,573,966; 4,610,662; 4,636,195; 4,655,746; 4,690,672; 4,824,436; 4,911,163; 4,976,733; 5,059,178; 5,090,960; 5,167,628; 5,195,955; 5,222,941; 5,370,609; 5,380,284; 5,443,446; 5,462,529; 5,496,267; 5,785,675; 5,833,650 and 5,951,458. Multi-lumen catheter devices are described in U.S. Pat. Nos. 4,329,994; 4,838,881; 5,149,330; 5,167,623; 5,207,648; 5,542,937; and 6,013,068.

SUMMARY OF THE INVENTION

Methods of enhancing fluid flow through a vascular site occupied by a vascular occlusion, as well as systems and kits for use in practicing the same, are provided. In practicing the subject methods, the vascular site is flushed simultaneously with a first dissolution fluid (e.g., an organic matter dissolution fluid and/or an inorganic matter dissolution fluid), and a second dissolution fluid attenuating fluid, where flushing is carried out in a manner such that only a surface of the vascular occlusion is contacted with the non-attenuated dissolution fluid. Examples of dissolution fluid/dissolution fluid attenuating fluid pairs include: (1) oxidizing agent fluid and fluid comprising oxidizable neutralizing agent; (2) surfactant fluid and phosphate buffered saline; (3) acidic solution and phosphate buffered saline; etc. Flushing is carried out in this manner for a period of time sufficient for fluid flow through the vascular site to be enhanced, e.g. increased or established. The subject methods, systems and kits for practicing the same find use in the treatment of a variety of different vascular diseases characterized by the presence of vascular occlusions, including both partial and total occlusions.

DESCRIPTION OF THE SPECIFIC EMBODIMENTS

Figure 1A:
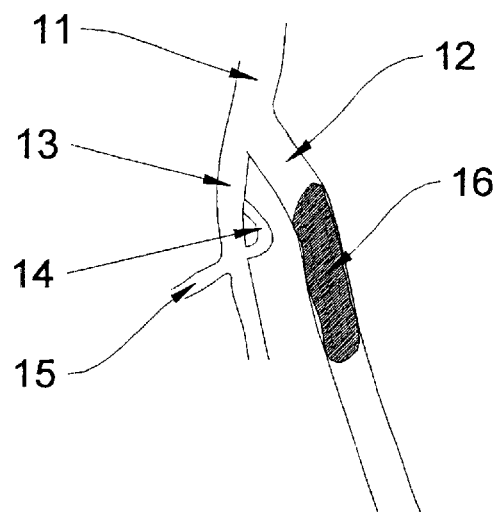
FIGS. 1A & 1B provide views of a totally occluded and partially occluded vascular site, respectively.

Methods for enhancing fluid flow through a vascular site occupied by a vascular occlusion, as well as systems and kits for use in practicing the same, are provided. In practicing the subject methods, the vascular site is flushed simultaneously with a first dissolution fluid and a second dissolution fluid attenuating fluid, where flushing is carried out in a manner such that only a surface of the vascular occlusion is contacted with the non-attenuated dissolution fluid. Examples of dissolution fluid/dissolution fluid attenuating fluid pairs include: (1) oxidizing agent fluid and fluid comprising oxidizable neutralizing agent; (2) surfactant fluid and phosphate buffered saline; (3) acidic solution and phosphate buffered saline; etc. Flushing is carried out in this manner for a period of time sufficient for fluid flow through the vascular site to be enhanced, e.g. increased or established. The subject methods, systems and kits for practicing the same find use in the treatment of a variety of different vascular diseases characterized by the presence of vascular occlusions, including both partial and total occlusions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

METHODS

As summarized above, the subject invention provides methods for enhancing fluid flow through a vascular site occupied by a vascular occlusion or lesion. By enhanced is meant that fluid flow is either established in situations where fluid flow is not initially present, e.g., where the target vascular occlusion is a total occlusion, or increased where some fluid flow through the vascular site is present, e.g., in situations where the vascular site is occupied by a partial occlusion. Where fluid flow is increased, the amount or magnitude of increase is generally at least about 1 fold, usually at least about 5 fold and more usually at least about 10 fold.

The Target Vascular Site

The target site through which fluid flow is enhanced by the subject methods is a site within a vessel, typically an artery or vein, and usually an artery. In many embodiments, the vascular site is a peripheral vascular site, by which is meant that the vessel in which the vascular site is located is a vessel found in one of the extremities of the patient to be treated, i.e., the arms or legs. Often, the vascular site is a site in a lower extremity vessel, e.g., a lower extremity artery. Thus, of particular interest in certain embodiments are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g., the aorta, a coronary artery or branch vessel thereof, etc. In yet other embodiments, the vascular site is present in a carotid artery or a branch vessel thereof.

The vascular site is occupied by a vascular occlusion in such a manner that fluid flow through the vascular site, e.g., blood flow, is at least impeded if not substantially inhibited. By at least impeded is meant that fluid flow is reduced by at least 20%, usually by at least 50% and more usually by at least 80% through the vascular site as compared to a control. In such situations, the vascular site is occupied by a partial vascular occlusion. By substantially inhibited is meant that substantially no fluid flows through the vascular site. For purposes of this invention, fluid flow through a vascular site is considered to be substantially inhibited where it is not possible to pass a guidewire through the vascular site, where the guidewire has a diameter ranging from 0.014 to 0.038 in and is applied to the site with a pressure ranging from about 1 to 30 oz.

Figure 1B:
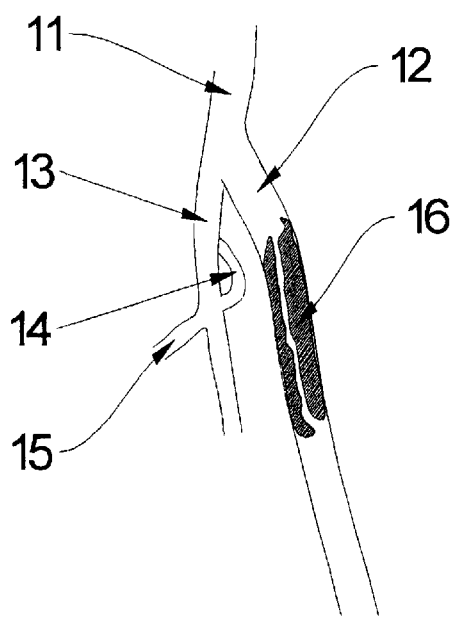

A representation of a peripheral artery having a vascular site occupied by a total vascular occlusion is provided in FIG. 1A while a representation of a peripheral artery having a vascular site occupied by a partial vascular occlusion is provided in FIG. 1B. In FIGS. 1A & 1B, the external iliac artery 11 is shown as it branches into the SFA 12 and the profunda 13. Also shown are the medial circumflex and the later circumflex, 14 and 15 respectively. The SFA is totally occluded by occlusion 16 in FIG. 1A and partially occluded by occlusion 16 in FIG. 1B.

The Target Vascular Occlusion

The vascular occlusion that occupies the target vascular site is generally a complex structure of two or more disparate components, where such components include both inorganic, e.g., calcium phosphate (such as dahllite) and organic components, including organic matter, e.g., lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. Thrombus may also be associated with the vascular lesion or occlusion. For example, in certain embodiments, one or both ends of the occlusion may be characterized by being primarily thrombotic material, e.g., a thrombus. The nature of the thrombotic domain may be organized or disorganized. As such, calcified occlusions that are targets of the subject methods include those that may be described as: type IV, type V and type VI lesions, as defined in Stary et al., Arterioscler. Thromb. Vasc. Biol. (1995)15:1512–1531.

In the vascular occlusions that occupy the target vascular sites of the subject methods, the size of the occlusion varies depending on location and specific nature of the occlusion. Generally, the volume of the occlusion ranges from about 20 to 10,000 mm$^3$, usually from about 30 to 500 mm$^3$ and more usually from about 50 to 300 mm$^3$.

Flushing the Vascular Occlusion

A feature of the subject methods is that the vascular site that includes the target vascular occlusion is simultaneously flushed with a dissolution fluid and a dissolution fluid attenuating fluid. By simultaneously flushed is meant that both a dissolution fluid and a dissolution fluid attenuating fluid are introduced to the vascular site at the same time and fluid is concomitantly removed from the vascular site in a manner such that only a surface of the vascular occlusion is contacted with non-attenuated dissolution fluid and the remainder of the vascular site is contacted with attenuated dissolution fluid. Flushing is also carried out in a manner such that the overall pressure in the vascular site remains substantially constant or isometric, i.e., such that substantially isobaric conditions are maintained in the vascular site during the flushing procedure.

In flushing the target vascular site according to the subject methods, the dissolution and dissolution fluid attenuating fluids (described in greater detail infra) may be introduced into the vascular site and fluid may be removed from the vascular site using any convenient protocol, so long as the method of fluid introduction and removal that is employed provides for the above parameters, i.e., dissolution fluid contact limited to a target occlusion surface and maintenance of substantially isobaric conditions. In many embodiments, a multi-lumen catheter based system is employed to flush the target vascular site, where the catheter based system includes at least two distinct lumens for introducing the dissolution and dissolution fluid attenuating fluids to the vascular site and a third lumen for removal of fluid from the vascular site, i.e., for aspiration of fluid (and debris when present) from the vascular site. In certain embodiments, the device may be a four lumen device, which is designed for delivery of two different dissolution fluids at the same time or at different times but through different lumens, e.g., the device may include an organic dissolution fluid lumen and inorganic dissolution fluid lumen. In such a device, in addition to the two distinct dissolution fluid lumens, there is the dissolution fluid attenuating solution lumen and the aspiration lumen such that the device has four distinct lumens. Representative multi-lumen catheter devices and systems that can be used to practice the subject methods are described in greater detail infra.

In flushing the target vascular sites with the dissolution fluid and dissolution fluid attenuating fluid, the fluids are introduced in a manner such that the flow rate of fluid through the vascular site of the lesion is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the occlusion or the volume of the target vascular site, as defined above. The total amount of dissolution fluid that is passed through the local environment of the lesion during the treatment period typically ranges from about 100 to 1000 cc, usually from about 200 to 800 cc and more usually from about 400 to 500 cc. The total amount of dissolution fluid attenuating fluid that is passed through the local environment typically ranges from about 100 to 1000 cc, usually from about 200 to 800 cc and more usually from about 400 to 500 cc. The fluids are generally pressurized to achieve the desired flow rate, as described supra. For example, in embodiments in which a multilumen catheter system is employed to deliver the fluids to the target vascular site, the pressure at the proximal end of the catheter assembly through which the fluids are introduced into the local environment typically ranges from about 50 to 1200 psi, usually from about 100 to 600 psi and more usually from about 200 to 400 psi. It is important to note that the overall pressure in the local environment is maintained at substantially isometric or isobaric conditions. As such, the negative pressure at the entrance to the aspiration means of the catheter system, e.g., the open annulus at the distal end of the aspiration catheter in a coaxial catheter system as described infra, will be of sufficient magnitude to provide for substantially isobaric conditions. Preferably, the overall pressure in the local environment is maintained at a value ranging from about 0.1 to 3 psi, usually from a bout 0.5 to 2.5 psi and more usually from about 1 to 2 psi.

As mentioned above, the dissolution fluid and dissolution fluid attenuating fluid are introduced into the target vascular site in a manner such that only a surface of the target vascular occlusion is contacted with non-attenuated dissolution fluid. As such, during practice of the subject methods, the remainder of the target vascular site is contacted with attenuated dissolution fluid, i.e. a mixture of dissolution fluid and dissolution fluid attenuating fluid. For example, where the target vascular occlusion is a total occlusion, the proximal surface of the total occlusion is contacted with non-attenuated dissolution fluid while the remainder of the target vascular site, e.g., the vessel walls proximal to the total occlusion, are contacted with attenuated dissolution fluid, i.e., a fluid that is a combination of both the dissolution fluid and the dissolution fluid attenuating fluid.

As mentioned above, in practicing the subject methods the target occlusion is flushed with the dissolution fluid and dissolution attenuating fluid in a manner such that the pressure in the target vascular site, i.e., local environment which includes the surface of the occlusion, e.g., the area bounded by the vessel walls, the surface of the target occlusion and the catheter system used to deliver the solution, remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, concomitant with fluid introduction into the target vascular site, fluid is simultaneously removed from the target vascular site or local environment comprising the surface of the target occlusion, such that the overall volume of fluid in the target vascular site or local environment remains substantially constant, where any difference in volume at any two given times during the treatment period does not exceed about 50%, and usually does not exceed about 10%. As such, the dissolution fluid is introduced into the local environment of the target lesion in a manner such that the local environment remains substantially isovolumetric.

Time Period

The surface of the target occlusion is contacted, e.g., flushed, with the dissolution fluid according to the protocols described above for a period of time sufficient for fluid flow to be enhanced or established through the vascular site, e.g., established or improved. As such, where the target occlusion is a total occlusion, contact is maintained for a period of time sufficient for a guidewire to be passed through the vascular site, as described above. Alternatively, where the target occlusion is a partial occlusion, contact is achieved for a period of time sufficient for the rate of fluid flow to be increased through the vascular site, generally by at least about 10%, usually by at least about 50%, and in many embodiments by at least about 100%. Generally, the period of time during which the surface of the occlusion is contacted with the dissolution solution ranges from about 5 to 100 minutes, usually from about 10 to 30 minutes. In certain embodiments, the contact duration typically lasts for a period of time ranging from about 5 to 30 minutes, usually from about 10 to 30 minutes and more usually from about 10 to 20 minutes.

Outcome

As discussed above, the subject methods result in the enhancement of fluid flow through the vascular site occupied by the occlusion. Fluid flow is considered to be enhanced in those situations where the vascular site is totally occluded when a guide wire can be moved through the vascular site without significant resistance. Fluid flow is considered to be enhanced in those situations in which the vascular site is partially occluded when the rate of fluid flow through the vascular site increases by at least 10%, usually by at least 50% and in many embodiments by at least 100%.

In certain embodiments, the subject methods will not result in complete removal of the target occlusion from the vascular site. As such, the vascular site, while not totally occluded, may still include lesion deposits on the wall which impede fluid flow through the vascular site and the removal or reduction of which is desired. Any convenient protocol for treating these remaining deposits may be employed, e.g., balloon angioplasty, atherectomy, stenting, etc. Also of interest is the use of two balloon catheters and an acidic dissolution solution, as described in 09/353,127; the disclosure of which is herein incorporated by reference.

Of particular interest in those embodiments where the vascular site is initially totally occluded and the partial and total occlusion catheter inserts describe infra are employed, fluid flow through the total occlusion is first established using the catheter assembly made up of the total occlusion catheter insert inside the aspiration catheter. Following establishment of fluid flow, the rate of fluid flow is increased using the catheter assembly made up of the partial occlusion catheter insert inside the aspiration catheter.

The above described basic protocol of the subject invention may be modified to include one or more additional steps, as described in greater detail below under the heading "Optional Features." However, prior to describing these representative optional features of the subject invention, the dissolution fluid and dissolution fluid attenuating fluid elements of the subject invention will now be described in greater detail.

FLUIDS EMPLOYED IN THE SUBJECT METHODS

As summarized above, in practicing the subject methods a target vascular site is flushed with both a dissolution fluid and a dissolution fluid attenuating fluid. As such, the target vascular site is concomitantly contacted with a dissolution fluid and a dissolution fluid attenuating fluid. The dissolution fluid and dissolution fluid attenuating fluid are now described separately in greater detail.

Dissolution Fluid

The dissolution fluid employed in the subject methods is one that, upon contact with the target occlusion or lesion, serves to dissolve and/or dislodge one or more components of the target lesion in a manner such that fluid flow is enhanced through the vascular site, as described above. The nature of the dissolution may vary greatly depending on the nature of the target occlusion or lesion and the nature of the component or components that are to be dissolved/dispersed/dislodged with the dissolution fluid. For example, the dissolution fluid may be a dissolution fluid which dissolves inorganic matter, e.g., calcium phosphate minerals, such as dahllite and the like. Alternatively, the dissolution fluid may be a fluid that dissolves organic matter, e.g., structures made up of lipids, proteins, whole cells and the like. In certain embodiments, the dissolution fluid may be one that dissolves both organic and inorganic matter, e.g., both calcium phosphate mineral and lipid/protein structures etc. In other words, it may be a solution that includes a component that dissolves organic matter and a component that dissolves inorganic matter, where these components may be the same or different. Representative dissolution fluids are now described in greater detail individually below.

Organic Matter Dissolution Fluids

Organic matter dissolution fluids include oxidizing or "bleach" solutions, surfactant solutions, enzymatic solutions, organic solvent solutions, and the like. Each of these types of solutions is described separately below.

Oxidizing Solutions

In this embodiment, the dissolution solution comprises one or more oxidizing agents that are capable of degrading the organic matter of the target lesion, and thereby facilitating its removal from the target site via the subject methods. Of interest as oxidizing agents are bleaching agents.

Bleaches of interest include halogen bleaches. Examples of such bleaches include, but are not limited to, alkali metal and alkaline earth salts of hypohalite, haloamines, haloimines, haloimides and haloamides. Hypochlorite and compounds producing hypochlorite in aqueous solution are preferred in certain embodiments, although hypobromite is also suitable in certain embodiments. Representative hypochlorite-producing compounds include sodium, potassium, lithium and calcium hypochlorite, chlorinated trisodium phosphate dodecahydrate, potassium and sodium dichloroisocyanurate and trichlorocyanuric acid.

Organic bleach sources suitable for use include heterocyclic N-bromo and N-chloro imides such as trichlorocyanuric and tribromocyanuric acid, dibromo- and dichlorocyanuric acid, and potassium and sodium salts thereof, N-brominated and N-chlorinated succinimide, malonimide, phthalimide and naphthalimide. Also suitable are hydantoins, such as dibromo- and dichloro dimethylhydantoin, chlorobromodimethyl hydantoin, N-chlorosulfamide (haloamide) and chloramine (haloamine). Particularly preferred in this invention is sodium hypochlorite having the chemical formula NaOCl.

Also of interest are peracids, including inorganic and/or organic peracids (percarboxylic acids) and/or peroxy compounds. Examples are alkali metal perborates or alkali metal carbonate perhydrates, especially the sodium salts. An example of an organic peracid which can be used is peracetic acid. More generally of interest are $C_{1-12}$-percarboxylic acids, $C_{8-16}$-dipercarboxylic acids, imidopercaproic acids or aryldipercaproic acids. Specific examples of acids which can be used are peracetic acid, linear or branched monoperoctanoic, -nonanoic, -decanoic or -dodecanoic acids, diperdecane- and -dodecanedioic acids, mono- and diperphthalic acids, -isophthalic acids and -terephthalic acids, phthalimidopercaproic acid (PAP) and terephthaloyl-diamidopercaproic acid (TOCAP). The percarboxylic acids can be used as free acids or as salts of the acids, preferably alkali metal or alkaline earth metal salts.

Also of interest as the oxidizing bleach agent are peroxy bleaching compounds. The peroxy bleaching compound may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable. Specific agents of interest include sodium perborate tetrahydrate, sodium perborate monohydrate, and sodium percarbonate. Another suitable hydrogen peroxide generating system is a combination of a $C_1$–$C_4$ alkanol oxidase and a $C_1$–$C_4$ alkanol. Alkylhydroxy peroxides are another class of peroxy bleaching compounds. Examples of these materials include cumene hydroperoxide and t-butyl hydroperoxide.

The concentration of the oxidizing agent in the solution, which is generally an aqueous solution, is sufficient to achieve the desired organic matter dissolution and may vary depending on the nature of the oxidizing agent. In many embodiments, the concentration of the oxidizing agent ranges from about 1 to 50%, usually from about 5 to 30% and more usually from about 10 to 30%. Where the oxidizing agent is hypohalite salt, e.g., sodium hypochlorite, the concentration of the oxidizing agent typically ranges from about 1 to 50%, usually from about 10 to 30%.

Surfactant Solutions

In surfactant solutions employed in the subject methods, surfactants of interest include both ionic, e.g. cationic, anionic (such as soaps) and zwitterionic, and nonionic surfactants. As such, of interest in many embodiments are soaps and detergents. Specific surfactants and detergents of interest include:

Cationic surfactants, such as polyquaternium-10, guar hydroxypropyltrimonium chloride, laurtrimonium chloride, cetrimonium chloride, laurtrimonium bromide, cetrimonium bromide, lauralkonium chloride, stearalkonium chloride, trimethylglycine, ditallowdimonium chloride, alkyl dimethyl benzylammonium chlorides and alkyl trimethylammonium methosulfate, Alkyltrimethylammonium Bromides, Cetyldimethylethylammonium Bromide, Benzalkonium Chloride, Cetylpyridinium Benzethonium Chloride, Decamethonium Bromide, Benzyldimethyldodecylammonium Bromide, Dimethyldioctadecylammonium Bromide, Benzyldimethylhexadecylammonium Bromide, Methylbenzethionium Chloride, Benzyldimethyltetradecylammonium Bromide, Methyltrioctylammonium Chloride, N,N',N'-Polyoxyethylene(10)-N-tallow-1,3-diaminopropane, and the like;

Anionic surfactants, such as naturally occurring anionic surfactant compounds or derivatives thereof, e.g. bile salts (cholic acid, dehydrocholic, deoxycholic, lithocholic, taurcholic acid, glycocholic acid, etc.,) as well as synthetic surfactants and detergents, e.g. sodium dodecyl sulfate, sodium lauroyl glutamate, sodium undecenyl glutamate, sodium cetyl glutamate, lauryl phosphate, cetyl phosphate, disodium laureth-3 sulfosuccinate, sodium cocoyl isethionate, sodium lauryl sulfate, sodium tetradecyl sulfate, sodium 2-ethylhexyl sulfate, sodium octylphenol glycolether sulfate, sodium dodecylbenzene sulfonate, sodium lauryldiglycol sulfate, ammonium tritertiarybutyl phenol and penta- and octa-glycol sulfonates, disodium n-octyldecyl sulfosuccinate, sodium dioctyl sulfosuccinate, sodium diisooctyl sulphosuccinate, acyl isethionates, acyl taurates, fatty acid amides of methyl tauride and acyl sarcosinates, Aerosol 22, Dioctyl Sulfosuccinate, Dodecyl Sulfate, Aerosol$^r$-OT, 1-Dodecansulfonic Acid, 1-Nonanesulfonic Acid, Alginic Acid*, Glycocholic Acid, 1-Octanesulfonic Acid, Caprylic Acid, Glycodeoxycholic Acid, 1-Pentanesulfonic Acid, 1-Decanesulfonic Acid, 1-Heptanesulfonic Acid, Taurocholic Acid, Dehydrocholic Acid, 1-Hexanesulfonic Acid, Taurodeoxycholic Acid, Deoxycholic Acid, N-Lauroylsarcosine, Tergitol and the like (*All acids are used as salts, usually sodium or potassium; **Bile acids), and the like;

Zwitterionic surfactants, e.g. CHAPS, lauramidopropyl betaine, cocamidopropyl betaine, cocamidopropyl hydroxysultaine, cocamidopropylamine oxide, lauryl betaine, lauryl hydroxysultaine, lauraminoxide, myristamine oxide, sodium lauroamphoacetate, sodium cocoamphoacetate and lauroamphocarboxyglycinate CHAPS$^+$, N-Octadecyl-N,N-dimethyl-3-ammonio-CHAPSO$^+$, 1-propanesulfonate N-Decyl-N,N-dimethyl-3-ammonio-N-Octyl-N,N-dimethyl-3-ammonio-1-propanesulfonate, 1-propanesulfonate N-Dodecyl-N,N-dimethyl-3-ammonio-Phosphatidylcholine, 1-propanesulfonate B-Tetradecyl-N,N-dimethyl-3-ammonio- N-Hexadecyl-N,N-dimethyl-3-ammonio-1-propanesulfonate, 1-propanesulfonate ($^+$Nondenaturing), and the like; and Non-ionic surfactants, e.g. nonoxynol-9, glycol monostearate, glycol distearate, PEG-150 distearate, methyl gluceth-10, methyl gluceth-20, methyl glucose sesquistearate, sodium PCA, polyethoxy 20 sorbitan monooleate, polyoxyethylene ethers and TRITON®, TERGITOL® and SURFYNOL™ surfactants, BIGCHAP, Decanoyl-N-methylglucamide, n-Nonyl α-D-glucopyranoside, n-Decyl-α-D-Glucopyranoside, n-Nonyl β-D-glucopyranoside, n-Decyl-β-D-Glupyranoside, Octanoyl-N-methylglucamide, n-Decyl-β-D-Maltopyranoside, n-Octyl α-D-Glucopyranoside, Deoxy-BIGCHAP, n-Octyl β-D-Glucopyranoside, n-Dodecyl-β-D-Glucopyranoside, Octyl β-D Thiogalactopyranoside, n-Dodecyl-α-D-Maltoside, Octyl β-D-Thioglucopyranoside, n-Dodecyl-β-D-Maltoside, Polyoxyethylene Esters, Heptanoyl-N-methylglucamide, Polyoxyethylene Ethers, n-Heptyl-β-D-Glucopyranoside, Polyoxyethylenesorbital Esters, n-Heptyl-β-D-Thioglucopyranoside, Sorbitan Esters, n-Hexyl-β-Dglucopyranoside, n-Tetradecyl β-D-Maltoside, Igepal CA-630, Tritons, 1-Monooleoyl-rac-glycerol, Nonanoyl-N-methylgluamide, Tyloxapol, n-Undecyl β-D-Glucopyranoside, Saponin, Nonidet P-40, Digitonin, and the like; etc.

Of particular interest in certain embodiments are naturally occurring anionic surfactant compounds or derivatives thereof, e.g. bile salts such as cholic acid, dehydrocholic, deoxycholic, lithocholic, taurcholic acid, glycocholic acid etc., and the like. In those embodiments where these agents are employed in the dissolution fluid, they may be obtained from any convenient source, including the patient's own gall bladder. In other words, they may be harvested from the gall bladder, processed as desired, e.g. to remove impurities, decrease the concentration etc, and then employed in the subject methods.

Where the dissolution fluid contains one or more surfactants, the overall surfactant concentration in the fluid will vary, depending on the nature of the particular surfactant employed.

The surfactant concentration of the dissolution fluid may vary greatly, depending on the nature of the surfactant employed, the nature of the target lesion, etc., but is sufficient to solubilize or disperse the target lesion to a sufficient extent for fluid flow to be enhanced through the vascular site. In many embodiments, the dissolution fluid is an aqueous surfactant solution in which the concentration of the surfactant is at least 0.01%, usually at least about 0.1%, where the surfactant concentration may be as high as 5% or 10% or higher, but often will not exceed about 10%.

Enzymatic Solutions

Instead of, or in addition to, a surfactant, the dissolution solution may include one or more enzymes for degrading various constituents of the target lesion, such as proteins, lipids, lipoproteins, and the like. Suitable enzymes include those selected from lipolytic, amylolytic and proteolytic enzymes. Proteolytic enzymes (proteases) which are of interest include those commercially available protease enzymes sold under the tradenames Alcalase and Savinase by Novo Industries A/S (Denmark) and Maxatase by International Bio-Synthetics, Inc. (The Netherlands). Amylolytic (amylase) enzymes (i.e. amylases) of interest include, for example, alpha-amylases obtained from a special strain of B licheniforms, described in more detail in GB 1,269,839 (Novo). Commercially available amylases include for example, Rapidase, sold by International Bio-Synthetics Inc, and Termamyl, sold by Novo Industries A/S. Lipolytic enzymes (i.e. lipases) which find use include phospholipases A, B, C, D and sphingomyelinase, and the like. Other such agents that may be included are thrombolytic agents, e.g. urokinase, tPA, and the like.

Organic Solvents

In yet other embodiments, the organic matter dissolution fluid may include one or more organic solvents, where the organic solvents employed in the subject methods are generally biocompatible, pharmaceutically acceptable and will at least partially dissolve the lipid component of the target lesion. Any convenient organic solvent may be employed.

Inorganic Matter Dissolution Fluids

Where it is desired to dissolve an inorganic component in the target vascular lesion, such as calcium phosphate mineral (e.g. dahllite) found in calcified vascular lesions or occlusions, acidic dissolution fluids are of particular interest. A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCL). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

Dissolution Fluids that Dissolve Both Organic and Inorganic Matter

Of interest in certain embodiments of the invention are dissolution fluids that are capable of dissolving both organic matter and inorganic matter. In these fluids, the fluid may contain one active agent that dissolves both organic and inorganic matter, or a first active agent(s) for dissolving organic matter and a second active agent for dissolving inorganic matter. An example of a dissolution fluid of this embodiments is a fluid that includes both a surfactant/detergent component and an acid, e.g. an anionic, cationic, zwitterionic or non-ionic surfactant in combination with an acidic dissolution fluid, where these components are described supra.

Of particular interest in many embodiments is the use of a hydrogen chloride solution that includes a surfactant. In these embodiments, the concentration of HCl in the solution ranges from about 0.001 to 1.0 N, usually from about 0.01 to 1.0 N and more usually from about 0.1 to 1.0 N. In many embodiments, the fluid will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl. The surfactant may be a cationic, anionic, zwitterionic or non-ionic surfactant, as described supra.

Of particular interest are aqueous hydrogen chloride solutions that consist of water, hydrogen chloride, a cationic surfactant, e.g., sodium dodecyl sulfate, and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M. In many embodiments, the concentration of sodium dodecyl sulfate ranges from about 0.01% to 10%, usually from about 0.1% to 5.0% and is often around 1%.

Dissolution Fluid Attenuating Fluids

As indicated above, the target vascular site is flushed in the subject methods with not only a dissolution fluid, such as one of the fluids described above, but also a dissolution fluid attenuating fluid. By dissolution fluid attenuating fluid is meant a fluid that at least reduces the ability of the one or more active agents present in the dissolution fluid to act on the target lesion, e.g., solubilize, disperse, etc. In other words, the attenuating fluid is a fluid that serves to at least impede the ability of the dissolution fluid active agent(s) to solubilize or disperse its target component in the target vascular occlusion. The manner or mechanism by which the attenuating fluid achieves this result may vary greatly depending on the active agent that is to be modulated by the attenuating fluid. As such, the nature of the attenuating fluid may vary greatly depending on the nature of the dissolution fluid that is to be attenuated. Representative attenuating fluids are now described in greater detail separately below.

Oxidizing Agent Attenuating Fluids

Where the active agent of the dissolution solution is an oxidizing agent, one type of attenuating fluid of interest is an aqueous fluid that serves to reduce the concentration of the oxidizing agent to a reduced level, e.g., 50%, 40%, 30%, 20%, 10% or lower. Aqueous fluids of interest include water, physiologically compatible aqueous solutions, e.g. saline, phosphate buffered saline, sodium bicarbonate solution, and the like.

Of particular interest are fluids that include one or more oxizable species that are capable of neutralizing the oxidizing agent of the dissolution fluid. Oxidizable species of interest include, but are not limited to, oxidizable ions, e.g., sulfur containing anions, such as metabisulfite, etc.; activated carbon sources, e.g, activated charcoal; and the like. Antioxidants such as ascorbic acid, oxidizable amino acid solutions such as methionine, cysteine, or protein solutions containing the same are also of interest. Free amino groups, sulfhydryl, and thioethers are all readily oxidized attenuating solutions. 5-amino-2,3-dihydro-1,4-phthalazine-dione or o-aminophthalylhydrazide (Luminol) is also useful as an oxidizable attenuating solution.

Surfactant Attenuating Fluids

Where the active agent of the dissolution solution is a surfactant, one type of attenuating fluid of interest is an aqueous fluid that serves to reduce the concentration of the surfactant agent to a level such that the rate of solubilization of lipids is reduced, if not substantially eliminated. Aqueous fluids of interest include water, physiologically compatible aqueous solutions, e.g. saline, phosphate buffered saline, sodium bicarbonate solution, and the like.

Enzyme Attenuating Fluids

In those embodiments where the active agent is an enzyme, the attenuating fluid may comprise one or more agents that reduces, if not eliminates, the catalytic activity of the enzyme. As such, the attenuating fluid may include one or more of denaturants, inhibitors, chelators, e.g. EDTA, that chelate ions necessary for enzyme activity, and the like.

Acid Attenuating Fluids

Where the dissolution fluid is an acidic dissolution fluid, the attenuating fluid is generally a pH elevating solution. By pH elevating solution is meant any solution that, upon combination with the acidic dissolution solution, produces a solution with an elevated pH with respect to the acidic dissolution solution. In principle, any fluid that, upon combination of with the acid dissolution fluid, produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiologically acceptable buffer solutions, etc., where in many embodiments, the pH elevating solution is a buffer solution. Representative buffer solutions of interest include: phosphate buffered saline, sodium bicarbonate and the like.

Representative Combinations of Dissolution Fluids and Dissolution Fluid Attenuating Fluids For purposes of further description of the subject invention, specific representative methods are now described in greater detail. Specifically, a representative method in which a calcified vascular occlusion that also includes organic matter is flushed first with an oxidizing agent dissolution fluid and then with an acidic dissolution fluid, where administration of each disparate oxidizing agent dissolution fluid is accompanied by a buffer attenuating fluid.

Vascular Calcified Lesion

For treatment of vascular calcified occlusions, a surface of the target vascular occlusion is flushed with first with an oxidizing agent dissolution fluid and then with an acidic dissolution fluid for a period of time sufficient for fluid flow to be to be enhanced through the vascular site. The subject methods are further characterized in that, simultaneously with the oxidizing dissolution fluid and acidic dissolution fluid, an attenuating fluid, e.g., phosphate buffered saline, is also introduced into the vascular site of the target lesion, i.e. the target vascular site. A feature of the subject methods is that both the dissolution fluids and the attenuating fluid are introduced to the target vascular site in a manner such that the dissolution fluids primarily contact the surface of the target occlusion, with the remainder of the target vascular site being contacted with fluid that has been attenuated, e.g. a lower concentration oxidizing agent, a pH which is much higher than that of the acidic dissolution fluid, etc. In other words, the dissolution fluids and attenuating fluids are introduced into the vascular site in a manner such that only the target vascular lesion is contacted with the full strength dissolution fluid. As such, the remainder of the target vascular site is contacted with a attenuated dissolution fluid, e.g. fluid that has a pH well above that of the acidic dissolution fluid, where the lowest pH to which the remainder of the target vascular site is subjected is not less than 4, preferably not less than 5 and more preferably not less than 6. In other words, only the target vascular occlusion is contacted with the full strength dissolution fluid while the remainder of the target vascular site is contacted with an attenuated fluid, e.g., a solution the pH of which is not less than 4, preferably not less than 5 and more preferable not less than 6.

Figure 4:
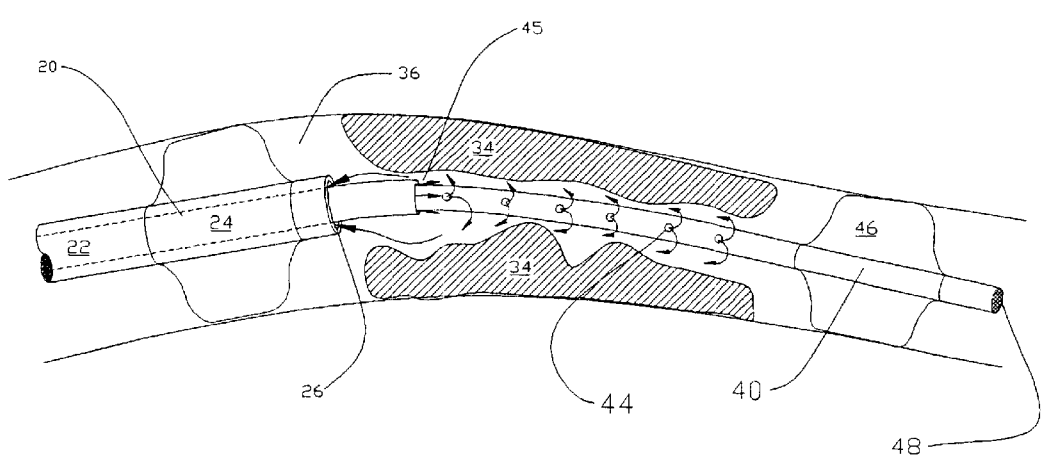
FIG. 4 provides a depiction of the use of the partial occlusion catheter system according to the subject invention.
Figure 6:
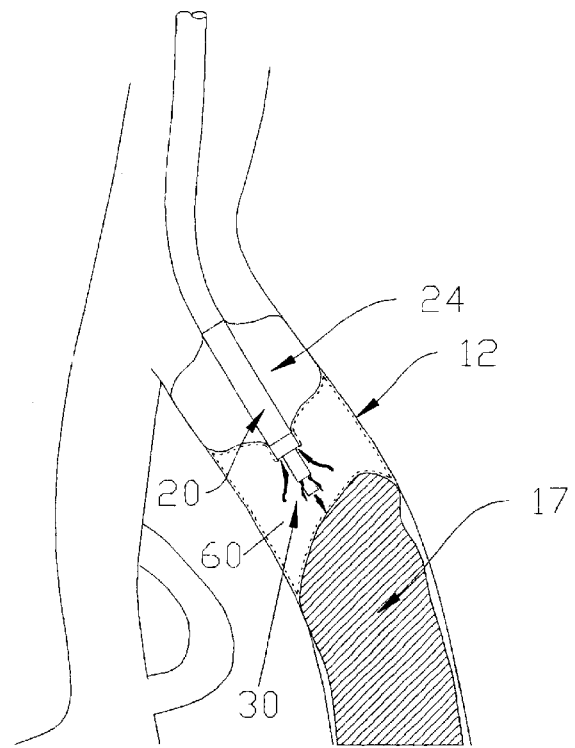
FIGS. 6 to 8 provides a representation of the various stages of the use of the total occlusion system of the subject invention.

A representation of a target vascular site being flushed with both a dissolution fluid and an attenuating fluid according to this embodiment of the subject methods is provided in FIGS. 4 and 6. In FIG. 4, where the target lesion is a partial occlusion, a coaxial partial occlusion catheter device is introduced into the vascular site such that the balloon 46 of the partial occlusion insert 40 and the balloon 24 of the aspiration catheter 20 flank the partial occlusion 34. Dissolution fluid is introduced by the plurality of ports 44 on the partial occlusion insert. An attenuating solution is concomitantly introduced through annular space 45. Fluid is then removed from the vascular site by the aspiration catheter 20 through annular space 26. FIG. 6 provides a view of a total occlusion catheter insert flushing a vascular site 12 of a total occlusion 17. As can be seen in FIG. 6, dissolution fluid is introduced through the central catheter and attenuating solution is introduced via the catheter immediately concentric with the center catheter. Fluid is removed from the vascular site via the aspiration catheter, in which the central and intermediate catheters are coaxially positioned. Another representation is provided in the Experimental Section, infra, which shows a dissolution agent concentration gradient which occurs in the vascular site during treatment according to the present invention.

Where the site is flushed first with an oxidizing dissolution fluid and then with an acidic dissolution fluid, the two types of fluids may be alternately delivered via the fluid delivery means, where alternate delivery may be provide by a valve or analogous means at the proximal end of the delivery lumen which alternates the type of dissolution fluid that enters the fluid delivery lumen.

OPTIONAL FEATURES OF THE SUBJECT METHODS

In a number of embodiments of the subject methods, the methods in which the surface of the target occlusion is contacted with the dissolution fluid may be modified to include a number of additional method steps. Additional method steps that may be present in the overall process include: rendering the local environment of the target occlusion bloodless, washing or rinsing the local environment of the target occlusion, applying external energy to the target occlusion; imaging the target vascular site; establishing or expanding a passageway through an initial thrombotic domain of the target occlusion; and the like. Each of these representative optional features is described separately below.

Rendering the Local Environment Bloodless

In many preferred embodiments, as described above, the local environment of the target occlusion is rendered substantially bloodless prior to introduction of the acidic dissolution fluid. Any convenient protocol for rendering the target vascular site substantially bloodless may be employed. For example, where balloon catheter systems are employed, such as those described below, the balloon(s) of the assembled catheter system is inflated to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution includes an anticlotting factor in many embodiments, where anticlotting factors of interest include heparin and the like. The washing solution can also contain chelating agents.

Application of External Energy

In certain embodiments, external energy is applied to the vascular site to promote mechanical break-up of the occlusion into particles or debris that can be easily removed from the vascular site. Any means of applying external energy to the vascular site may be employed. As such, jets or other such means on a catheter device which are capable of providing varying external forces to the occlusion sufficient to cause the occlusion to break up or disrupt may be employed. Of particular interest in many embodiments is the use of sonic energy, where sonic energy of interest includes infrasound, audible sound and ultrasound. The sonic energy, e.g., ultrasound, can be applied during the entire time of contact of the cardiovascular tissue with the acidic treatment solution, or it can be applied for only part of the treatment period. In one embodiment, the sonic energy is applied for several short periods of time while the dissolution treatment solution is contacted with the target occlusion. Sonic energy applications devices that are suitable for use with the subject methods are known and readily available to those of skill in the art. For example, there are several devices for the application of ultrasound to cardiovascular tissue known to those of skill in the art. See e.g. U.S. Pat. No. 4,808,153 and U.S. Pat. No. 5,432,663, the disclosures of which are herein incorporated by reference.

In such methods where external energy is applied to the occlusion in order to disrupt or break-up the occlusion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the vascular site. Particles may be removed from the vascular site using any convenient means, such as the catheter of the subject invention described in greater detail infra.

Another means that may be employed to apply external energy to the lesion during the dissolution process is to use a mechanical means of applying external energy. Mechanical means of interest include moving structures, e.g., rotating wires, guidewires, rotating blades or burrs, etc., which physically contact the target occlusion and thereby apply physical external energy to the target lesion. See e.g. FIGS. 9 and 10. A catheter as disclosed in U.S. Pat. No. 5,358,472, the disclosure of which is herein incorporated by reference, or analogous thereto may be employed.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Thrombus Removal Step

The subject methods may further include a thrombus removal step, e.g. where the domain of the target occlusion is covered by a thrombotic domain, as described above. In such methods, any thrombus removal means that is capable of providing sufficient access of the dissolution solution to the surface of the target lesion may be employed. Thus, where the thrombotic domain is a disorganized domain, it may be sufficient to pass increasingly larger diameter guidewires through the domain until a passageway of sufficient width to provide access of the catheter assembly described above to the surface of the occlusion is established. Alternatively, portions of the thrombotic domain may be removed, e.g. via atherectomy methods, angioplasty methods, and the like, where devices for performing such procedures are known to those of skill in the art. See the patent references cited in the Relevant Literature section, supra, which references are herein incorporated by reference.

Use of a Plurality of Solutions

In many embodiments, the subject methods include contacting the surface of the target occlusion with a plurality, i.e., two or more distinct solutions, at least one of which is a dissolution solution as described above. Where one or more additional distinct solutions, such as priming solutions, washing solutions, and the like are employed, as described below, such disparate solutions are generally introduced sequentially to the vascular site. For example, the target occlusion may be contacted with the following order of solutions: (1) washing solution to render the local environment substantially bloodless; (2) organic phase dissolution solution, e.g. detergent solution such as cholic acid solution, to remove organic phases from the target lesion; (3) acidic dissolution solution to demineralize the target occlusion; and (4) washing solution. Other sequences of solution application can also be employed. See U.S. patent application Ser. No. 09/353,127, the disclosure of which is herein incorporated by reference. Alternatively, where two different dissolution solutions are employed in tandem, e.g., with a multilumen catheter having a two or more disparate dissolution fluid lumens capable of delivering two different dissolution fluids at the same time. Generally, in any method where a plurality of different solutions are contacted with the target occlusion, each dissolution fluid is administered in conjunction with a corresponding dissolution fluid attenuating solution.

ADDITIONAL APPLICATIONS

In addition to methods of enhancing fluid flow through a target vascular site, methods and devices are also provided for reducing the mineral content of non-intimal tissue, as described in copending application Ser. No. 09/382,571, the disclosure of which is herein incorporated by reference. Specifically, the subject invention provides methods and devices that are analogous to those disclosed in the copending application, with the only difference being that the target tissue is contacted simultaneously with both a dissolution fluid and dissolution fluid attenuating fluid, e.g. an acidic dissolution solution and a pH elevating solution. As such, the devices are modified such that a means for introducing a pH elevating solution at the same time as the acidic dissolution solution to the target tissue is provided.

CATHETER DEVICES

As mentioned above, catheter devices and systems are employed in many embodiments of the subject invention. In many embodiments where catheter devices are employed, the catheter devices and systems are multilumen structures which are designed to flush a vascular site with a dissolution fluid and dissolution fluid attenuating fluid in a manner that provides for enhancement of fluid flow through a vascular site that is at least partially, if not totally, occluded by a vascular lesion, particularly a vascular calcified lesion. In these embodiments, the multi-lumen catheter devices comprise at least three distinct lumens, i.e. the subject devices at least include a first, second and third lumen.

A representative multi-lumen catheter system that includes at least three lumens and is specifically designed for use with an acidic dissolution fluid is now described in greater detail. (Note that analogous systems are suitable for use with non-acidic dissolution fluids, e.g. surfactant dissolution fluids). The first lumen is characterized in that it has at least an inner wall that is resistant to reaction with the dissolution fluid. For example, where the dissolution fluid is an acidic dissolution fluid, the first lumen has at least an inner wall that is resistant to reaction with the acidic dissolution solution, at least for a period of time sufficient for the intended use of the catheter to be completed. More specifically, at least the inner wall of the catheter is fabricated from a material that is resistant to reaction with a solution having a pH of less than about 4, preferably less than about 2 and more preferably less than about 1. As such, it must be inert to a solution that has a pH from about 0 to 4.

Generally, the material from which the inner surface of the first lumen is fabricated must be resistant to reaction with the dissolution fluid, e.g. must be substantially inert with respect to the dissolution fluid, for a period of time that is at least about 10 min long, preferably at least about 20 min long and more preferably for at least about 1 hour long or longer. Materials of interest from which at least the inner surface of the first lumen may be fabricated include: biocompatible polymers, e.g. polyimide, PBAX™, polyethylene, and the like. The thickness of the inner surface of the first lumen must be sufficient to protect the remainder of the catheter device from any corrosive reaction with the acidic dissolution solution that is conveyed or delivered through the first lumen during use of the catheter device, as described in greater detail infra. As such, the thickness of the inner wall is typically at least about 0.5 mm, usually at least about 0.1 mm and more usually at least about 0.25 mm. The first lumen of the subject multi-lumen catheter devices is further characterized in that it is capable of being attached in fluid communication, either directly or indirectly, with a dissolution fluid reservoir. The effective total cross sectional area through which dissolution fluid flows during use of the subject devices, (i.e. the total cross-sectional areas of any openings present at the distal end of the first lumen less any area occupied by a blocking element positioned in any of the openings) is sufficient to provide the requisite rate of flushing of the vascular occlusion with the dissolution fluid. Generally, the effective total cross sectional area provided by the at least one opening at the distal end of the first lumen is at least about 0.1 mm$^2$, often at least about 0.2 mm$^2$ and somtimes at least about 0.3 mm$^2$, where the total effective cross sectional area at the distal end of the first lumen may be as large as 0.6 mm$^2$ or larger, but in certain embodiments will not exceed about 0.5 mm$^2$ and in other embodiments will not exceed about 0.4 mm$^2$.

The second lumen of the subject catheter device is employed to convey or deliver the dissolution fluid attenuating fluid, e.g. a pH elevating fluid, such as a buffer, to a vascular site, as described in greater detail infra. As such, the second lumen of the subject multi-lumen catheter devices is characterized in that it is capable of being attached in fluid communication, either directly or indirectly, with a dissolution fluid attenuating fluid reservoir. The effective total cross-sectional area of the opening at the distal end of the second lumen, where effective total cross-sectional area is as defined above (e.g. the annular space in a coaxial embodiment, as described in greater detail infra), is sufficient to provide the requisite amount of attenuating fluid to the vascular site so that any portion of the vascular site apart from the target surface of the vascular solution is not contacted with a non-attenuated fluid, e.g. an acidic dissolution fluid which has a pH of less than about 4, preferably less than about 5 and more preferably less than about 6. Accordingly, the effective cross-sectional area of the opening(s) of the distal end of the second lumen is at least about 0.8 mm$^2$, usually at least about 1.4 mm$^2$ and may be as larger as 2.2 mm$^2$ or larger, but generally does not exceed about 2.0 mm$^2$ and usually does not exceed about 1.5 mm$^2$.

The third lumen of the subject multi-lumen catheter devices is an aspiration lumen. The aspiration lumen is characterized by at least having a distal opening(s) with an effective total cross-sectional area (e.g. the area of the annular space in the coaxial embodiments described infra) that is sufficiently large to remove fluid, and debris, from the vascular site at substantially the same rate that fluid (e.g. buffer solution and acidic dissolution solution) is introduced into the vascular site during use of the device, such that the fluid pressure in the vascular site remains substantially isobaric or isometric, where by substantially isobaric or isometric is meant that the fluid pressure in the vascular site does not vary by more than about 50 mm Hg, preferably does not vary by more than about 10 mm Hg, and more preferably does not vary by more than about 5 mm Hg over the total flushing period.

The subject catheter devices are further characterized in many embodiments by at least including a first vascular occlusion means positioned at some point proximal to the distal end of the outer surface of the catheter device, e.g. the outer surface of the aspiration catheter in the coaxial embodiments described infra. By vascular occlusion means is meant any device or component that is capable of substantially, and preferably completely, occluding a vessel, e.g. an artery or vein. By substantially occluding is meant that fluid, e.g. blood, flow past the occlusion means upon activation is reduced by at least 95%, usually by at least 97% and more usually by at least 99%, where in preferred embodiments, fluid flow is reduced by 100% such that the fluid flow into the vascular site is substantially, if not completely, inhibited. Any convenient means may be employed, where a vascular occlusion means of particular interest includes an inflatable balloon. Inflatable balloons are well known in the catheter art, and any convenient balloon configuration may be employed. While the inflatable balloon may be one that is designed to be inflated with a gas or liquid, of particular interest in many embodiments are those that are configured to be inflated with a liquid, e.g. a pH elevating solution.

In certain embodiments, the delivery catheters include at least two disparate dissolution fluid lumens, in addition to the dissolution fluid attenuating fluid lumen and the aspiration lumen. As such, in these embodiments, the subject delivery catheters may include four lumens, where the lumens may be arranged to provide for optimal delivery or removal of fluid consistent with their intended purpose.

Specific Alternative Embodiments

The subject invention provides a number of distinct alternative embodiments of the subject catheter devices and systems. One preferred specific embodiment of interest is a coaxial embodiment, in which each of the first, second and third lumens are coaxial. Other alternative embodiments include embodiments in which at least one of the lumens is not coaxial with the other lumens, as well as embodiments in which none of the lumens is coaxial. Each of these representative alternative embodiments is now described in greater detail below.

Coaxial Embodiments

As mentioned above, a preferred embodiment of the subject multi-lumen catheter devices is a coaxial embodiment, in which the first, second and third lumens of the subject catheter device are coaxial. By "coaxial" is meant that the first, second and third lumens share a common axis. As such, in these embodiments the first lumen is present in an element positioned inside the second lumen, which in turn is present in an element positioned inside the third lumen. Generally, the first, second and third lumens are found inside fluid delivery means which are positioned inside one another, where the fluid delivery means are often elongated tubular elements. The coaxially positioned fluid delivery means comprising the first, second and third lumens, i.e. the first, second and third fluid delivery means, may be held in a static relationship with respect to one or another or may be movable with respect to one another, such that at least one of the fluid delivery means, and preferably at least two of the fluid delivery means may be moved without moving the other fluid delivery means—i.e. each of the first, second and third fluid delivery means may be moved independently of one another. Spacers or other means on the inner walls of at least the second and third lumens may be present to maintain the coaxial configuration.

In this coaxial embodiment of the subject invention, one of the lumens serves to deliver an acidic dissolution fluid, one of the lumens serves to deliver a pH elevating fluid and one of the lumens serves to remove fluid from the vascular site. In other words, two of the lumens serve to introduce fluid to the vascular site and one of the lumens serves to remove fluid from the vascular site. While any of the lumens may serve any of the above functions, generally, the first lumen which delivers the acidic dissolution solution (i.e the one that has at least an inner surface that is substantially inert to the acidic dissolution fluid) is the innermost lumen of the coaxial lumens of the device. As such, the first lumen is the lumen with the inner walls that are closest to the center line or axis of the coaxial catheter device.

The first lumen is generally positioned along the center line or axis of a first elongated fluid delivery means, where the fluid delivery means generally extends along the length of the catheter from its proximal to distal end. The fluid delivery means is typically tubular in shape, and may have a variety of different cross-sectional configurations, including square, triangular, trapezoidal, circular, elliptical, irregular, and the like, where often the cross-sectional shape of the elongated tubular member is curvilinear, and more often is circular.

The design of the first fluid delivery means may vary depending on the nature of the target vascular occlusion, e.g. whether the target vascular occlusion is a total occlusion or a partial occlusion. The total occlusion first fluid delivery means, e.g. the total occlusion catheter insert, is an elongated tubular structure, as described above, having a blunt ended, open distal end through which fluid may be flowed under pressure. The length of the total occlusion catheter insert generally ranges from about 90 to 210 cm, usually from about 100 to 190 cm and more usually from about 110 to 150 cm. The outer diameter of the total occlusion catheter insert is such that the catheter insert may be slidably positioned in the second lumen (i.e. the lumen of the second fluid delivery means, as described infra), and typically ranges from about 0.4 to 2.0, usually from about 0.4 to 1.6 mm. The inner diameter of the total occlusion catheter insert typically ranges from about 0.2 to 1.0, usually from about 0.25 to 1.0 and more usually from about 0.3 to 1.0 mm.

Where the target occlusion is a partial occlusion, a partial occlusion first fluid delivery means is employed, i.e. a partial occlusion catheter insert. The partial occlusion catheter insert differs from the total occlusion catheter insert in a number of ways. First, the partial occlusion catheter insert includes a balloon or analogous vessel occlusion means at its distal end, where the distance between the vascular occlusion means and the distal end of the catheter insert typically ranges from 1 to 30 mm, usually from about 10 to 20 mm. Second, the partial occlusion vascular insert has one or more fluid introduction ports proximal to the proximal side of the distal balloon. The diameter of the infusion ports may vary, but typically ranges from about 0.2 to 1.2, usually from about 0.4 to 1.0 and more usually from about 0.5 to 0.8 mm. Where the vascular occlusion means on the partial occlusion catheter insert is a balloon, a balloon inflation lumen is also present in the partial occlusion catheter insert. Finally, the end of the partial occlusion catheter insert is sealed. The length of the partial occlusion catheter insert generally ranges from about 90 to 250 cm, usually from about 100 to 230 cm and more usually from about 110 to 190 cm. The outer diameter of the partial occlusion catheter insert is such that the catheter insert may be slidably positioned in the second lumen, i.e. the lumen of the second fluid delivery means, as described infra. The outer diameter typically ranges from about 0.5 to 2.0. The inner diameter of the partial occlusion catheter insert typically ranges from about 0.2 to 1.0, usually from about 0.25 to 1.0 and more usually from about 0.3 to 1.0 mm.

Figure 2B:
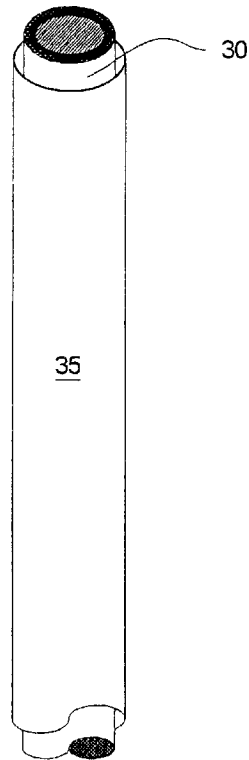
Figure 3:
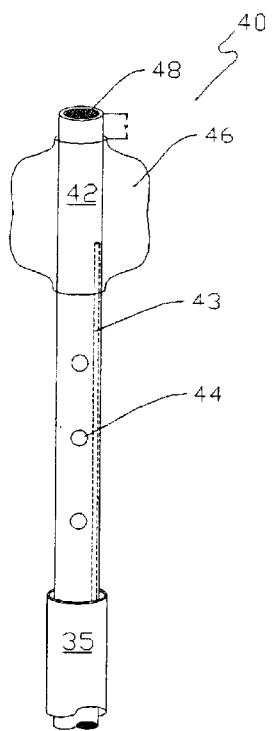
FIG. 3 provides a representation of a partial occlusion catheter insert for use in the aspiration catheter of FIG. 2A.

The above described partial and total catheter inserts are further characterized by being capable of being attached at their proximal ends, either directly or through one or more attachment means, to a fluid reservoir, e.g. an acidic dissolution fluid reservoir and, in the case of the partial occlusion catheter insert, a balloon inflation means. A representation of a total occlusion catheter insert 30 according to the subject invention is provided in FIG. 2B. A representative partial occlusion catheter insert is provided in FIG. 3. In FIG. 3, partial occlusion catheter insert 40 includes elongated tubular structure 42 that is sealed at its distal end 48. Proximal to the distal end 48 is balloon 46, where the distance Y typically ranges from about 1 to 30 mm, usually from about 10 to 20 mm. Also depicted are infusion ports 44. The diameter of the infusion ports may vary, but typically ranges from about 0.2 to 1.2, usually from about 0.4 to 1.0 and more usually from about 0.5 to 0.8 mm. Also shown is balloon inflation lumen 43, where the balloon inflation lumen has dimensions similar to those of balloon inflation lumen 23. As evidenced, the partial occlusion catheter insert includes two lumens, a fluid introduction lumen and a balloon inflation lumen. Also visible in FIGS. 2B and 3 is second delivery means 35 which includes the second lumen, described in greater detail below.

The second lumen of the subject multi-lumen catheter devices is designed for delivery of an attenuating fluid, e.g. a pH elevating solution, to the vascular site of the target occlusion. This lumen is generally present in a second fluid delivery means (element 35 in FIGS. 2B and 3), where the fluid delivery means is generally an elongated tubular structure analogous to the first fluid delivery means described supra. In the present coaxial embodiment, the dimensions of this second fluid delivery means, i.e. second catheter insert, are such that the first fluid delivery means or catheter insert described above (i.e. either the partial or total occlusion catheter insert) can fit inside this second fluid delivery means, i.e. can fit inside the lumen of the second fluid delivery means. A further limitation is that the first fluid delivery means must fit inside the second fluid delivery means in a manner such that an annular space is formed in the second lumen which is sufficient to convey the requisite amount of pH elevating fluid to the vascular site during use of the device. As such, the inner diameter of the second lumen exceeds the outer diameter of the first fluid delivery means by at least about 0.6 mm, sometimes at least about 0.9 mm and in certain embodiments at least about 1.2 mm. Accordingly, the inner diameter of the second fluid delivery means ranges from about 0.8 to 2.5, usually from about 0.9 to 1.9 and more usually from about 1.0 to 1.3 mm. The second fluid delivery means has an open distal end which, when positioned around the first fluid delivery means during use, forms an annular opening through which pH elevating fluid flows out of the second fluid delivery means and into the vascular site during use. The total effective cross-sectional area of the annular opening typically ranges from about 0.6 to 2.6, usually from about 0.8 to 1.9 and more usually from about 0.9 to 1.3 mm$^2$. The overall length of the second fluid delivery means typically ranges from about 90 to 210, usually from about 100 to 190 and more usually from about 110 to 150 cm. The second fluid delivery means is further characterized by having a means for connecting to a pH elevating fluid reservoir, either directly or indirectly, at its proximal end.

The first and second lumens and their respective fluid delivery means may be combined into integrated catheters in certain embodiments.

The third lumen in this coaxial embodiment of the subject devices is the outermost lumen, which is generally present in an elongated tubular structure analogous to the first and second fluid delivery means, as described above. The third lumen present in this third fluid delivery means is employed to remove fluid from the vascular site. As such, this third fluid delivery means is properly viewed as an aspiration catheter. The aspiration catheter is generally an elongated tubular structure fabricated from a flexible, biologically acceptable material having a balloon or analogous vessel occlusion means positioned at its distal end. The length of the aspiration catheter may vary, but is generally from about 80 to 200 cm, usually from about 90 to 180 cm and more usually from about 100 to 140 cm. The outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). The aspiration catheter is characterized by having an open distal end, where the inner diameter at the open distal end is sufficient to house the first and second coaxial fluid delivery means, as described supra, and remove fluid from the vascular site at the desired rate, e.g. a rate that provides for substantially isometric or isobaric pressure in the vascular site during treatment, through the resultant annular space. The inner diameter of the third or aspiration lumen, at least at its distal end and generally along the entire length of the aspiration catheter, typically ranges from about 0.2 to 2.0, usually from about 0.25 to 1.75 and more usually from about 0.35 to 1.5 mm. The total effective cross-sectional area at its distal end, i.e. the cross-sectional area of the annular space at the distal end opening, typically ranges from about 1.3 to 3.9, usually from about 1.3 to 3.2 and more usually from about 1.3 to 2.5 mm$^2$. Also present at the distal end of the aspiration catheter is a vessel occlusion means, where the vessel occlusion means is usually an inflatable balloon. The balloon is one that is inflatable to a volume sufficient to substantially occlude the vessel in which the aspiration catheter is positioned, e.g. by pressing against the intimal surface of the vessel in which the aspiration catheter is positioned. The balloon is in fluid or gaseous communication with an inflation lumen that runs the length of the aspiration catheter and can be connected to a balloon inflation means. The inflation lumen has an inner diameter that typically ranges from about 0.1 to 0.5, usually from about 0.2 to 0.4 mm. In certain embodiments, the aspiration catheter further includes a separate guidewire lumen. When present, the guidewire lumen has a diameter ranging from about 0.2 to 1.0 mm, usually from about 0.3 to 0.6 mm. Thus, the aspiration catheter includes at least two distinct lumens, i.e. an aspiration lumen (also referred to herein as the third lumen) and a balloon inflation lumen, and in many embodiments includes three distinct lumens, i.e. an aspiration lumen, a balloon inflation lumen and a guidewire lumen.

The aspiration catheter is further characterized by being capable of attaching, either directly or through one or more attachment means, at its proximal end to vacuum means, e.g. a negative pressure means, where such means is sufficient to provide for the desired aspiration during use of the device, and a balloon inflation means, where such means is sufficient to inflate the balloon at the distal end of the catheter when desired.

Figure 2A:
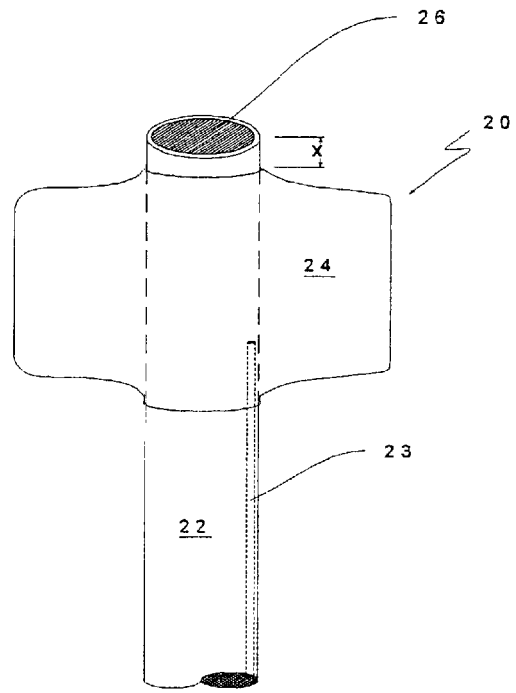
FIG. 2A provides a representation of an aspiration catheter according to an embodiment of the subject invention while FIG. 2B provides a representation of a total occlusion catheter insert for use in the aspiration catheter of FIG. 2A.

A representation of the aspiration catheter of the subject catheter systems found in the subject kits is provided in FIG. 2A. In FIG. 2A, aspiration catheter 20 includes elongated tubular member 22 and balloon 24 located proximal to the distal end. The distance X between the distal most portion of the balloon 24 and the distal end of the catheter typically ranges from about 1 to 20, usually from about 5 to 10 mm. Also shown is distal open end 26 through which either the partial or total occlusion insert catheter is moved and fluid is aspirated. Balloon 24 is inflatable via balloon inflation lumen 23.

Alternative Embodiments

In an alternative embodiments of the subject invention, at least two of the first, second and third lumens are not coaxial. In these alternative embodiments, the configuration of the first, second and third lumens in the device may vary greatly. For example, the first second and/or third lumens may be present on separate non-coaxial fluid delivery means. As such, the device could be made up of three different fluid delivery means bundled together to produce a triple lumen catheter device. Alternatively, a single fluid delivery means could house all three lumens. In certain embodiments, two of the lumens, i.e. the first and second lumen, will be present on a first fluid delivery means, which fluid delivery means is coaxially positioned within the third lumen. The first or internal fluid delivery means housing the first and second lumens may take on a variety of configurations. In one configuration, the first and second lumens terminate or open at the distal end of the internal fluid delivery means. In other configurations, one of the lumens opens at a different area from the other lumen. In these embodiments, the first lumen typically opens at the distal end of the internal fluid delivery means and the second lumen opens at a site proximal to the distal end of the internal fluid delivery means. The second lumen may open up at a one or more openings proximal to the distal end of the internal fluid delivery means. In each of these embodiments, the internal fluid delivery means housing the first and second lumens is present in a third lumen which is also housed by a fluid delivery means, where this fluid delivery means may be referred to as an aspiration catheter, as described above.

Other representative multilumen catheter devices that may be adapted for use in the subject methods include those described in U.S. Pat. Nos.: 329,994; 4,838,881; 5,149,330; 5,167,623; 5,207,648; 5,542,937; and 6,013,068; the disclosures of which are herein incorporated by reference. Where it is desired to apply mechanical energy to the target lesion in combination with flushing with a dissolution fluid and aspiration, a devices as disclosed in U.S. Pat. No. 5,358,472, the disclosure of which is herein incorporated by reference, or analogous thereto, may be employed.

CATHETER SYSTEMS

Also provided by the subject invention are systems for practicing the subject methods, i.e. for enhancing fluid flow through a vascular site occupied by a vascular occlusion. The subject systems at least include the catheter systems as described above, a manifold, a fluid reservoir for storing dissolution fluid, a fluid reservoir for attenuating fluid and a negative pressure means for providing aspiration or suction during use of the system. The systems may further include a number of optional components, e.g. guidewires, pumps for pressurizing the dissolution fluid, and the like. See e.g. U.S. patent application Ser. No. 09/384,860, the disclosure of which is herein incorporated by reference.

Figure 5:
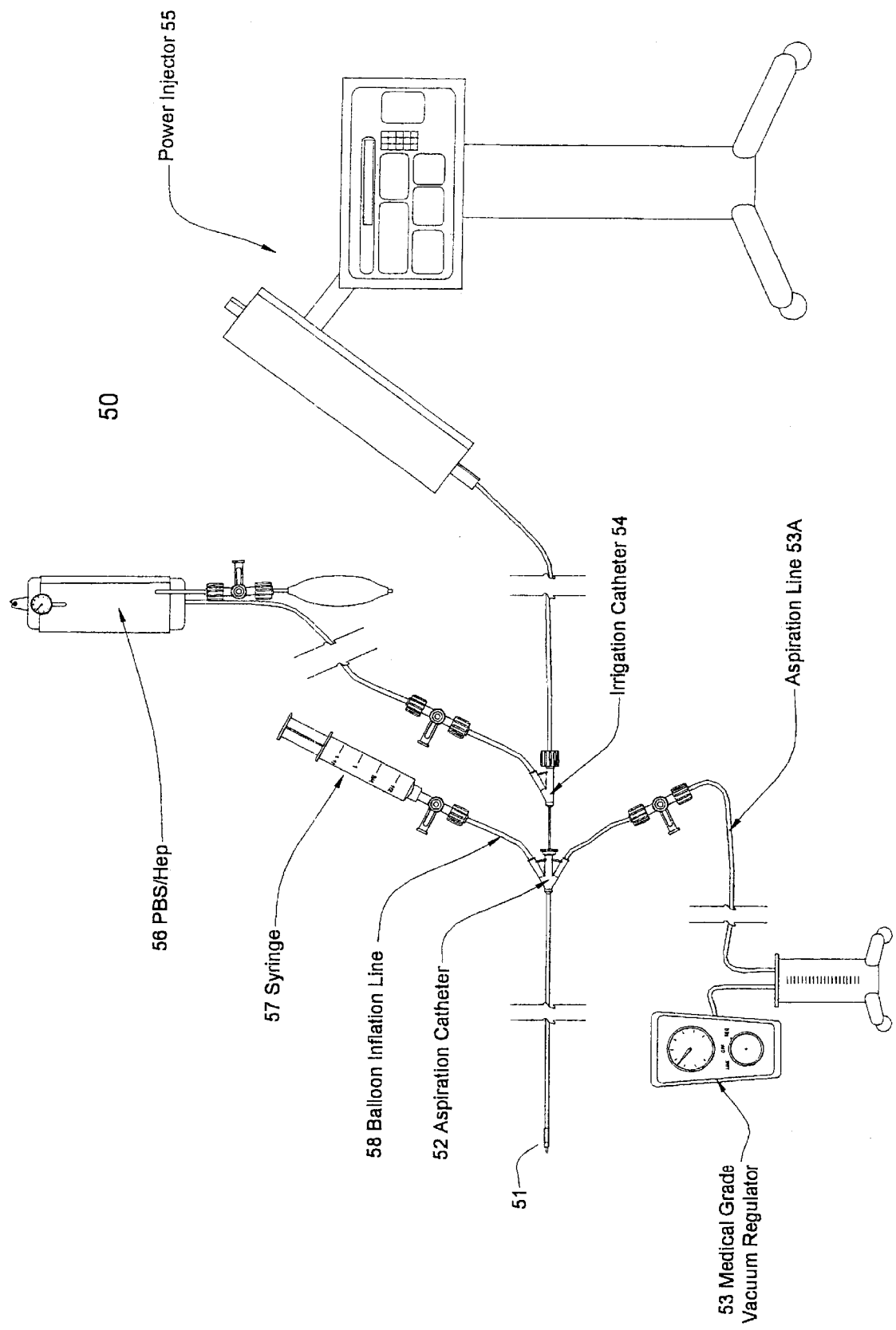
FIG. 5 provides a representation of a system according to the subject invention, which system includes a catheter device, manifold, fluid reservoirs, etc.

A representative system is provided in FIG. 5. In FIG. 5, system 50 is characterized by having catheter device 51 in fluid communication with the various fluid and vacuum sources require to practice the methods as described above. Specifically, the outer aspiration catheter 52 of the catheter device 51 is in communication with a medical grad vacuum regulator and vacuum means 53 by aspiration line 53A. The central or irrigation catheter 54 of the catheter device 51 is in fluid communication with power injector source of acidic dissolution solution, 55. The intermediate catheter of the catheter device 51 is in fluid communication with a source of pH elevating solution 56, e.g. PBS/Hep. Finally, syringe 57 is used to inflate the balloon of the catheter device via the balloon inflation line 58.

UTILITY

The subject devices and methods find use in a variety of different applications in which it is desired to enhance fluid flow, usually blood flow, (or at least pass a guidewire through), a vascular site that is occupied by a vascular occlusion, e.g. a partial or total occlusion. As such, the subject methods and devices find use in the treatment of peripheral vascular disease, etc. The subject methods also find use in the treatment of coronary vascular diseases. By treatment is meant that a guidewire can at least be passed through the vascular site under conditions which, prior to treatment, it could not. Treatment also includes situations where the subject methods provide for larger fluid passageways through the vascular site, including those situations where fluid flow is returned to substantially the normal rate through the vascular site. The subject methods may be used in conjunction with other methods, including balloon angioplasty, atherectomy, and the like, as part of a total treatment protocol.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

One specific application in which the subject methods find use is in the treatment of a host suffering from a vascular disease associated with the presence of vascular lesions. Such vascular diseases include diseases in which one or more different lesions are present on one or more locations of the vascular tissue of the host, where the lesion(s) may be present on a vessel wall, on a valve, etc.

By treatment is meant at least a reduction in a parameter of the disease, where parameter may include typical symptoms indicative of occluded vessels or malfunctioning valves, e.g. chest pains, angina, limb ischemia, etc., or risk factors associated with the disease or condition, e.g. narrowing of arteries, and the like. Treatment also includes situations where the host is cured of the vascular disease, i.e. where the lesion is completely removed.

The subject invention finds use in a number of specific representative applications. These applications include: peripheral atherectomies; coronary atherectomies; and valve/annular lesion removal. Each of these applications is discussed in greater detail separately below.

Peripheral Atherectomy

One type of specific method provided by the subject invention is a peripheral atherectomy, in which a target lesion present in a peripheral vessel, e.g. artery or vein, of the circulatory system is at least reduced in size if not removed. The target lesion may be present in any peripheral vessel, where the subject methods are particularly suited for use in the reduction/removal of lesions that are present in the renal, iliac, femoral, arteries, arteries of the lower extremities, and A-V access sites.

In peripheral atherectomy procedures according to the subject invention, the target calcified lesion is typically flushed with a dissolution solution according to the subject invention for a sufficient period of time for the desired reduction/removal of the target lesion to occur. The manner in which the target lesion is flushed with the solution generally depends on the nature of the device that is employed, as well as the nature of the target lesion. For example, one may cannulate the vessel on either side of the lesion, with the upstream cannula being used to introduce the dissolution solution and the downstream cannula being used to remove solution from the vessel. In these embodiments, isolation of the limb comprising the target peripheral vessel may be indicated, as described above. Alternatively, a catheter device that provides for a substantially sealed local environment of the target lesion may be employed to introduce and remove the dissolution solution from the site of the target lesion. These procedures are particularly suited for the treatment of target lesions that do not substantially occlude the peripheral vessel.

The above procedure may be used by itself in a given treatment process, where reduction/removal of the target lesion is sufficient to achieve the desired outcome of the particular therapy indicated by the host's condition. Alternatively, the above procedure may be used in combination with additional treatment modalities, including balloon angioplasty; stenting; mechanical atherectomy; bypass and the like, where the subject method of performing a peripheral atherectomy serves to prepare the target lesion and vessel for the subsequent treatment. Thus, the subject methods find use in: facilitating the placement of balloon catheters in narrow, focal, lesions; facilitating the placement of stents in narrow, focal, lesions; treating total peripheral vascular occlusions; and facilitating surgical bypass by removing lesions at proximal and/or distal anastomotic sites or converting procedures to percutaneous procedures.

Coronary Demineralizing Atherectomy

Another type of specific method provided by the subject invention is a coronary atherectomy, in which a target lesion present in a vessel associated with the heart, e.g. coronary artery, is at least reduced in size, if not removed. The target lesion may be present in any coronary vessel, such as the aorta, coronary arteries, etc. In coronary atherectomy procedures according to the subject invention, the target lesion is typically flushed with a dissolution solution according to the subject invention for a sufficient period of time for the desired reduction/removal of the target lesion to occur. The manner in which the target lesion is flushed with the solution generally depends on the nature of the device that is employed, as well as the nature of the target lesion. For example, where the coronary vessel is not totally occluded by the target lesion, a catheter device that provides for a substantially sealed local environment of the target lesion may be employed to introduce and remove the dissolution solution from the site of the target lesion. Importantly, the rate of inflow and outflow of fluid from the site of the target lesion is kept substantially constant so that pressure is not substantially elevated at the site of the target lesion. This process results in a steady decrease in the size of the target lesion, at least to a point where the lesion does not substantially completely occlude the target vessel.

The above procedure may be used by itself in a given treatment process, where reduction/removal of the target lesion is sufficient to achieve the desired outcome of the particular therapy indicated by the host's condition. Alternatively, the above procedure may be used in combination with additional treatment modalities, including balloon angioplasty; stenting; mechanical atherectomy; coronary artery bypass and the like, where the subject method of performing a coronary atherectomy serves to prepare the target lesion and vessel for the subsequent treatment. Thus, the subject methods find use in: facilitating the placement of balloon catheters in narrow, focal, lesions of coronary vessels; facilitating the placement of stents in narrow, focal, lesions of coronary vessels; treating total peripheral vascular occlusions in coronary vesels; and facilitating coronary vessel surgical bypass by removing lesions in proximal and/or distal anastomotic sites or converting procedures to percutaneous procedures.

Valve/Annulus Demineralization

Yet another application in which the subject methods find use is in the lesion reduction/removal of valves and/or annuli, typically those found in the heart or vessels closely associated therewith, e.g. the aortic valve, mitral annuli, etc. In other words, the subject methods are useful in valvuloplasties or annuloplasties, where a lesion present on a valve or annulus structure is reduced in size, if not removed. The valve/annular structure that is treatable according to the subject methods may be endogenous to the host or bioprosthetic, i.e. an implant, where the implant may be a allogenic, xenogeneic, synthetic, etc.

In at least reducing, if not removing, a lesion from a valve/annular structure according to this particular application of the subject invention, the valve or structure having the lesion present thereon is typically flushed with a dissolution solution, as described above. In many embodiments, the local environment of the valve/annular structure is substantially isolated from the remainder of the host's circulatory system during this flushing step. A variety of different devices may be employed to flush the structure with the dissolution solution, including that shown in FIG. 4 described supra, that disclosed in U.S. Pat. No. 5,167,628 the disclosure of which is herein incorporated by reference, and the like.

Valvuloplasties and annuloplasties according to the subject invention can be used to achieve a number of different therapeutic goals, including: (a) extension of the useful life of bioprosthetic implants; (b) enhancing the efficacy of annuloplasty ring placement; (c) decreasing the calcification of native heart valves, thereby delaying valve replacement; and the like.

KITS

Also provided by the subject invention are kits for use in enhancing fluid flow through a vascular site occupied by an occlusion. The subject kits at least include a catheter device or system, as described above. The kits may further include one or more additional components and accessories for use with the subject catheter systems, including tubing for connecting the various catheter components with fluid reservoirs, syringes, pumping means, etc., connectors, one or more guidewires, dilators, vacuum regulators, etc.

In certain embodiments, the kits further include one or more solutions, or precursors thereof, where in such embodiments the kits at least include dissolution fluid, such as an acidic dissolution fluid, e.g. a hydrochloric acid solution, an oxidizing fluid, a surfactant fluid, etc., as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 0.5 to 500 liters, usually from about 0.5 to 200 liters and more usually from about 0.5 to 100 liters. In many embodiments, the amount of dissolution fluid in the kit ranges from 0.5 to 5 liters, usually from about 0.5 to 2.0 liters and more usually from about 0.5 to 1.5 liters. Alternatively, the kit may comprise precursors of the dissolution solution for use in preparing the solution at the time of use. For example, the precursors may be provided in dry form for mixing with a fluid, e.g. water, at the time of use. In addition to the dissolution fluid or precursors thereof, the kit may further comprise a dissolution fluid attenuating fluid, e.g., a fluid containing an oxidizing agent neutralizing component, a pH elevating fluid, such as phosphate buffered saline, etc. Furthermore, the kits may also include one or more additional fluids (or dry precursors thereof), such as a priming solution, a washing solution, contrast medium, and the like.

Other elements that may be present in the subject kits include various components of the systems, including manifolds, balloon inflation means, e.g. syringes, pumping means, negative pressure means, guidewires, fluid delivery means, e.g., catheters and components thereof, etc.

In addition to above mentioned components, the subject kits typically further include instructions for using the components of the kit to flush a vascular site with two different fluids, e.g., to flush a vascular site with a dissolution fluid and a dissolution fluid attenuating fluid. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example I

In Vitro Cholesterol Dissolution

A. Introduction:

In vitro experiments were performed to document the efficacy of cholesterol dissolution using a variety of surfactants.

B. Methods:

Dissolution of cholesterol was examined in different solutions of bile salts, non-ionic, and ionic surfactants. Solutions of bile salts were prepared as follows: 0.5% solutions of cholic, dehydrocholic, deoxycholic, lithocholic acids were made by dissolving 0.5 grams of the free acid powders in 100 mL $H_2O$ previously adjusted to pH=12 with sodium hydroxide. Solutions were then adjusted to pH=7.5 with HCl. 1% surfactant solutions were made by dilution of concentrated stock solutions: Benzalkonium chloride, nonoxynol-9, sodium dodecyl sulfate, were prepared immediately prior to use. Dissolution studies were performed by adding 0.1 grams cholesterol powdered crystals to 50 mLs of the above surfactants with agitation on a rocker table for 1 hour. Solutions were then examined under light microscopy 200× magnification and cholesterol crystal presence or absence and crystal morphology recorded for each solution.

C. Results:

All solutions acted as dispersive agents for cholesterol crystals. Sodium dodecyl sulfate (SDS) was the most effective in solvating as no free crystals were observed 5 minutes after cholesterol addition. Benzalkonium chloride also appeared to dissolve most of the crystalline cholesterol although not as quickly as SDS as there were still crystals apparent after 10 minutes with approximately 50% crystal dissolution by 1 hour. Nonoxynol-9 had little or no observable effect on the crystal structure. The bile salts were effective in dispersing the cholesterol however crystal morphology was only slightly changed after 1 hour in solution; crystal edges and sharply defined faces appeared to round and soften.

D. Conclusions:

These results indicate that chemical dissolution of a major organic constituent of atherosclerotic plaque (cholesterol) is feasible using common surfactants and that dispersive agents such as bile salts are also effective in loosening plaque components for subsequent removal. It can also be safely extrapolated that lipid dissolution is readily achievable based on solubility data for lipids versus cholesterol.

Example II

In Vitro Thrombus Removal

A. Introduction:

In vitro experiments were performed to document the efficacy of thrombus removal using the common surfactant sodium dodecyl sulfate.

B. Methods:

Fresh cadaveric femoral arteries which contained soft clots partially occluding the vessel lumen were used. Flow was significantly reduced in all vessel segments prior to treatment with SDS as demonstrated by the inability to inject saline through the vessel using a 25 cc syringe.

Vessels were treated with a 1% surfactant solution of sodium dodecyl sulfate (SDS, Sigma chemicals), prepared immediately prior to use. Treatment consisted of injection of surfactant through a 35 cc male luer syringe and flow characteristics recorded.

C. Results:

SDS was effective in removing soft thrombus from occluded femoral arteries. Flow was reestablished in all samples and segments of clot were visible in the effluent of the flushed vessels. Approximately 60 cc of surfactant solution was used per treatment over a 10 minute interval.

D. Conclusions:

These results indicate that chemical removal of an organic constituent of atherosclerotic plaque (thrombus) is feasible using common surfactants and that some portions of clot may be dispersed for subsequent removal.

III. Demineralizing a Calcified Aorta

A. Materials

A human heart with an attached aorta and carotid artery branches was obtained and characterized flouroscopically for the presence of mineralization. The mineralized deposits are radio-opaque and are well-established to be the calcium phosphate mineral carbonated apatite (dahllite) [see Tomasic 1994 In: Brown and Constantz, Hydroxyapatite and Related Materials CRC Press]. Physical manipulation of the tissue indicated that the mineral makes the vessel rigid and the walls of the vessel are hard. Extensive mineralization was seen in the aorta and the three carotid artery branches. Two of the three side branches of the brachial-cephalic carotid artery were completely occluded with mineralization. The other two carotid artery branches were partially occluded with mineralization.

B. Experimental Set-up

The distal and proximal ends of the aorta were cannulated and tubing was attatched. The distal outflowing tube has a "Y-donnector" to allow the efluent solution to flow into two different collection traps: one for demineralizing solution, the other for saline wash. The reason for this design is that the calcium concentration is measured in the efluent demineralizing solution so it needs to be isolated from the occasional saline wash to remove contrast media. An infusion catheter was placed through the wall of the proximal tubing and advanced into the aorta to just proximal of the brachio-cephalic carotid branch point. The efluent ports of the unoccluded carotid arteries and the distal aortic tube were clipped off with hemostats and contrast media was infused into the infusion catheter under fluoroscopy, filling the aorta with radio-opaque contrast media. The extent of occlusion was quantified fluoroscopically. The hemostats were then unclipped and the system was flushed with saline.

C. Demineralization 4 liters of 1N hydrochloric acid with 0.25 mole/liter sodim chloride concentration were infused through the infusion catheter by drawing the demineralizing solution into 60 ml syringes with lure-lock cannulae, attaching them to the infusion catheter and injecting at a rate ranging between 125 and 250 ml/minute. Four successive infusion segments were performed:

0–5 minutes
5–10 minutes
10–15 minutes
15–20 minutes

Between each five minute infusion the system was flushed with saline, the open efluent ports were clipped with hemostats, radio-opaque contrast media was infused and the extent of mineralization quantified fluoroscopically. Following this evalution the hemostats were unclipped and the system flushed with saline and the next infusion begun.

D. Results

By the end of the experiment when all four liters of demineralizing solution had been infused, all three totally occluded sub-branches of the brachiocephalic carotid artery had been opened and solution flowed from their distal ports.

1. 0–5 minutes (approximately 550 ml)

The solution flowed out of the two partially occluded carotid arteries and the distal aortic tube was clipped off. About 2 minutes into the infusion, solution began dripping from the totally occluded brachio-cephalic segments. When the collected efluent demineralizing solution was observed, removed solids were collected in a 50 ml centrifuge vial; approximately 20 ccs of solid white material was present. The radio-contrast at 5 minutes showed the occluded arteries opening up and the lumen of all the arteries opening. The general extent of mineralization was also noticeably diminished.

2. 5–10 minutes (approximately 1 liter)

Now the most open carotid artery was clipped off, the partially occluded carotid artery was half clipped off, allowing limited out flow and the distal aortic tube was totally clipped-off. Flow progressively increased from the brachio-carotid arteries and two of the three sub-segments began flowing substantially, as did the partially occluded third carotid artery. Radio-contrast imaging at 10 minutes corroborated the flow observations, showing the arterial lumen had considerably opened to allow flow.

3. 10–15 minutes (approximately 1 liter)

Now both open carotid arteries were clipped off, allowing limited out flow through the brachial-cephalic carotid artery and the distal aortic tube was totally clipped-off. Flow progressively increased from the brachio-carotid artery and two of the three sub-segments began flowing substantially and third sub-segment began flowing somewhat. Radio-contrast imaging at 15 minutes corroborated the flow observations, showing the arterial lumen had considerably opened to allow flow.

4. 15–20 minutes (approximately 1.5 liters)

Now both open carotid arteries were clipped off as well as the two flowing brachio-cephalic sub-segments, allowing limited out flow through one brachial-cephalic sub-segment that was most occluded at the beginning and was still only flowing in a restricted fashion. The distal aortic tube was totally clipped-off. Flow progressively increased from the brachio-carotid sub-segment and began flowing to the extent that the flow squirted off the table onto the floor. Radio-contrast imaging at 20 minutes treatment corroborated the flow observations, showing the arterial lumen had considerably opened to allow flow.

E. Conclusion

By the end of the experiment, a heavily calcified aorta and carotid tree was substantially demineralized and flow re-established. The aorta changed from being hard to soft and resiliant to the touch. The vascular tissue showed no mechanical loss of strength or flexible behavior.

Example IV

Solution Containing Surfactant and Acid Components

A solution of sodium dodecyl sulfate (SDS) (a.k.a. sodium lauryl sulfate) (1%) and 0.1N hydrochloric acid (pH 1.0) made isotonic (300 mOsmol) with sodium chloride was prepared and compared with a solution of sodium dodecyl sulfate solution (1%). It was found that the sodium dodecyl sulfate solution and the sodium dodecyl sulfate/hydrochloric acid solution adjusted to pH 1.0 formed micelles around cholesterol crystals making the cholesterol crystals water soluble. These results indicate that an detergent/acid combination solution can be used to dissolve/remove both the mineral and organic components of a plaque simultaneously. Addition of the detergent to the hydrochloric acid solution does not affect the ability of the solution to dissolve mineral or the surfactant to dissolve the organic matter by forming micelles. This combination solution can be buffered with sodium bicarbonate ($NaHCO_3$) in the same manner that the hydrochloric acid solution is buffered with $NaHCO_3$, as described in the specification supra.

Example V pH Gradient Study

Materials/Method:

An Orion Needle-Tip electrode was used to measure pH. A 10 cm piece of ¼" ID Tygon tubing served as a vessel model. A hemostat was used to ligate the tubing to mimic a total occlusion. The pH electrode was inserted horizontally through the wall of the tubing just proximal to the ligation and pH measurements were made in the center of the tube and at both walls. The Corazon Total Occlusion Catheter/Aspiration Catheter system was inserted at the open end of the Tygon tubing and advanced to the pH electrode. The distance between the tip of the Total Occlusion Catheter and the tip of the Aspiration catheter was set at 5 mm. CDS was irrigated using a Medrad at 0.35 mL/s. Buffer was irrigated using an Endoflator (inflation device) at a pressure of 50–100 psi giving a flow rate of 0.22 mL/s. Aspiration was set at 150 torr. Initially, the distance between the catheter and the electrode, referred to as D, was 0 mm. Measurements were made at D=0, and then the catheter/aspiration system was withdrawn until the distance from the electrode was D=3 mm. Measurements were made for D=0, 3, 6, 9, 12, and 15 mm.

Results/Conclusion

The pH gradients measured are shown in the figure below. The numbers below represent an average of the pH values measured at that particular distance D from the tip of the catheter. The pH levels measured at the wall of the vessel are very similar on both sides

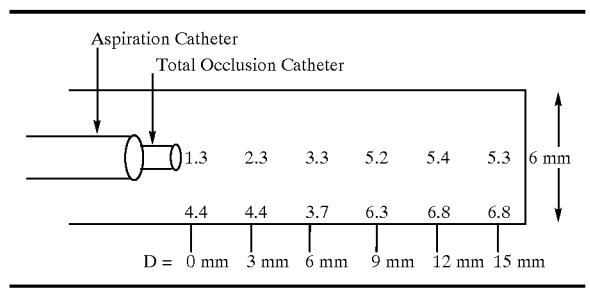

The figure shows that the pH rises as the distance from the tip of the catheter increases. The pH levels appear to reach an asymptote at a distance of about 9 mm from the tip of the catheter in both the center of the tube and at the walls. We have determined that cell hemolysis begins at around pH 4.0. The pH measurements taken at the walls of the tubing indicate that the walls are sufficiently buffered at all distances D. The dissolution of carbonated hydroxyapatite (CHA) occurs at a reasonable rate (~5 mg/min) at pHs below 1.3. Therefore, the tip of the catheter should be placed directly on CHA for dissolution, or at least proximal thereto.

Example VI

Safety

The following experiment was performed to evaluate the Safety and Feasibility of calcium demineralization solution via local delivery system in the peripheral arterial system. Safety was evaluated in terms of:

1) systemic response and toxicity (serum indices for renal and liver function, acid-base balance, blood chemistry and blood clotting factors if necessary)
2) cellular response of the treated vessel to both the demineralizing solution and the catheter delivery system.
3) end organ toxicity and tissue response via histopathology analysis of heart, liver, and kidneys.

Feasibility was assessed in terms of the following quantitative and qualitative assessments:

1) anatomical and morphological characteristics of the vessels via imaging angiography and intravascular ultrasound
2) functional measure of blood flow through the treated vessel assessed via transonic flow probe.

Methods: Canines were treated with Corazon Technologies' Decalcification System, Peripheral Arterial Catheter. This system is designed to simultaneously deliver two solutions: a demineralizing solution and a buffer. A third lumen is used simultaneously to aspirate the resulting mixture. Animals were randomly chosen and treated according to the following technique: (1) Bilateral exposure of the animal's femoral arteries, (2) Introducer and catheter insertion via an 8.5 Fr carotid puncture, advancing to left or right femoral artery (randomly chosen), (3) Temporary vessel loop ligature on distal femoral artery to represent total occlusion (4) "treatment" of total occlusion using demineraling solution and buffer, (5) removal of vessel loop, (6) repositioning of catheter to remaining femoral artery, (7) Temporary vessel loop ligature on distal femoral artery to represent total occlusion (8) treatment of total occlusion using saline (control), (9) removal of vessel loop, and (10) surgical closure and recovery of animal. Animals were recovered for 30, 60, or 90 days.

Results: Eight dogs were treated. Six animals were sacrificed at 0, 30 (n=3), 37, and 60 days. Microscopic pathology analysis indicates no difference between treated vessels and controls. Systemic and organ study results are pending. Noninvasive test results (ultrasound) of other surviving dog arteries indicate bilateral patent vessels.

Example VII

Representative Treatment Protocol

A. A 50 year old male having a total occlusion in the superficial femoral is treated as follows.

Figure 7:
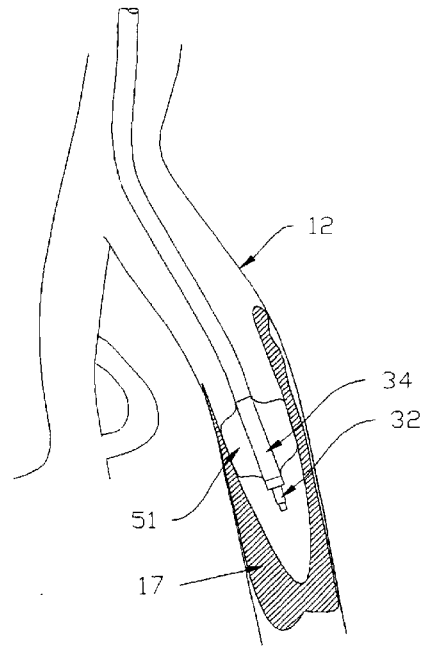
Figure 8:
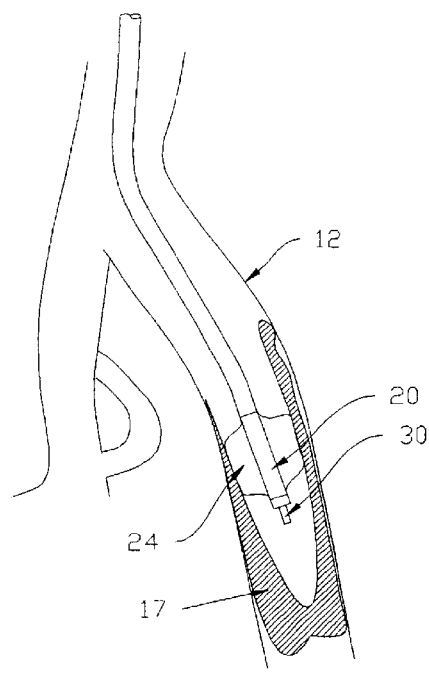

1. The patient is heparinized using standard procedures.
2. An introducer sheath is placed either in the same leg to provide retrograde access or in the opposite leg to provide cross-over access.
3. A guidewire is inserted and advanced to the site of the total occlusion.
4. The catheter device is inserted so that the distal end of the device is at the vascular site occupied by the total occlusion. The balloon is then inflated by depressing the syringe, such that the balloon occludes the vessel proximal to the occlusion. See FIG. 6.
5. Contrast medium is then injected into the vascular site to confirm the location of the distal end of the catheter and the inflated balloon.
6. A sufficient amount of heparinized phosphate buffered saline is then injected through port into the isolated vascular site or local environment and aspirated therefrom such that the isolated local environment is rendered substantially bloodless.
7. The surface of the total occlusion is then flushed with both an acidic dissolution fluid A (0.1N HCl, 0.05 M NaCl) and a phosphate buffered saline solution at the same time as shown in FIG. 6.
8. As the occlusion is demineralized, the catheter insert is advanced independent of the aspiration catheter and buffer catheter.
9. Where desired, the balloon may be deflated, the entire device repositioned, and then balloon may be reinflated to move the distal end of the total occlusion catheter insert to a site further into the occlusion. See FIGS. 7 and 8.
10. Once a passage through the occlusion sufficient to pass a guidewire through the occlusion is produced, the device is removed.
11. The above procedure results in fluid flow through the vascular site occupied by the lesion being reestablished, as evidenced by passing a guidewire through the vascular site.
12. Where desired, following reestablishment of fluid flow through the total occlusion, the total occlusion catheter insert is removed. A guidewire is then inserted through the large lumen of aspiration catheter 20 to a space beyond the distal end of the occlusion. A partial occlusion catheter insert is then introduced over the guidewire to a position such that the balloon at the distal end of the insert is on the far side of the partial occlusion. The vascular site is then flushed as shown in FIG. 4 until the desired amount of lesion dissolution is achieved.

B. Variations on the Above Procedure

Figure 9:
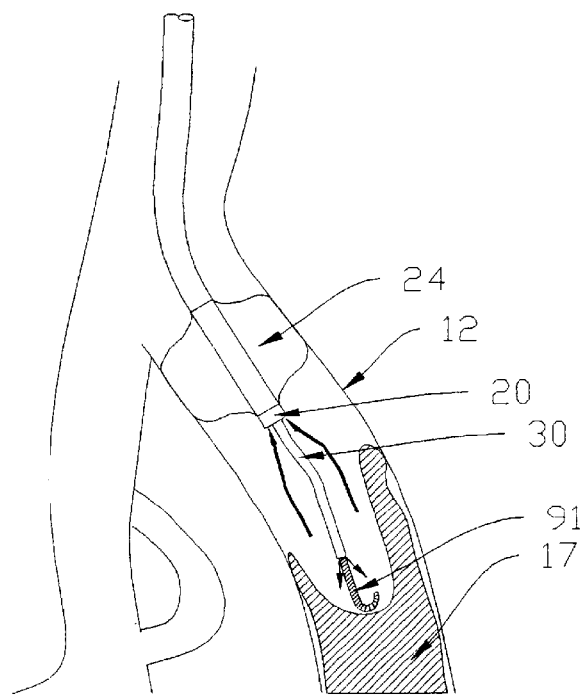
FIGS. 9 and 10 provide views of alternative embodiments of the subject methods in which external energy is applied to the occlusion, e.g. by movement of a guidewire as shown in FIG. 9.
Figure 10:
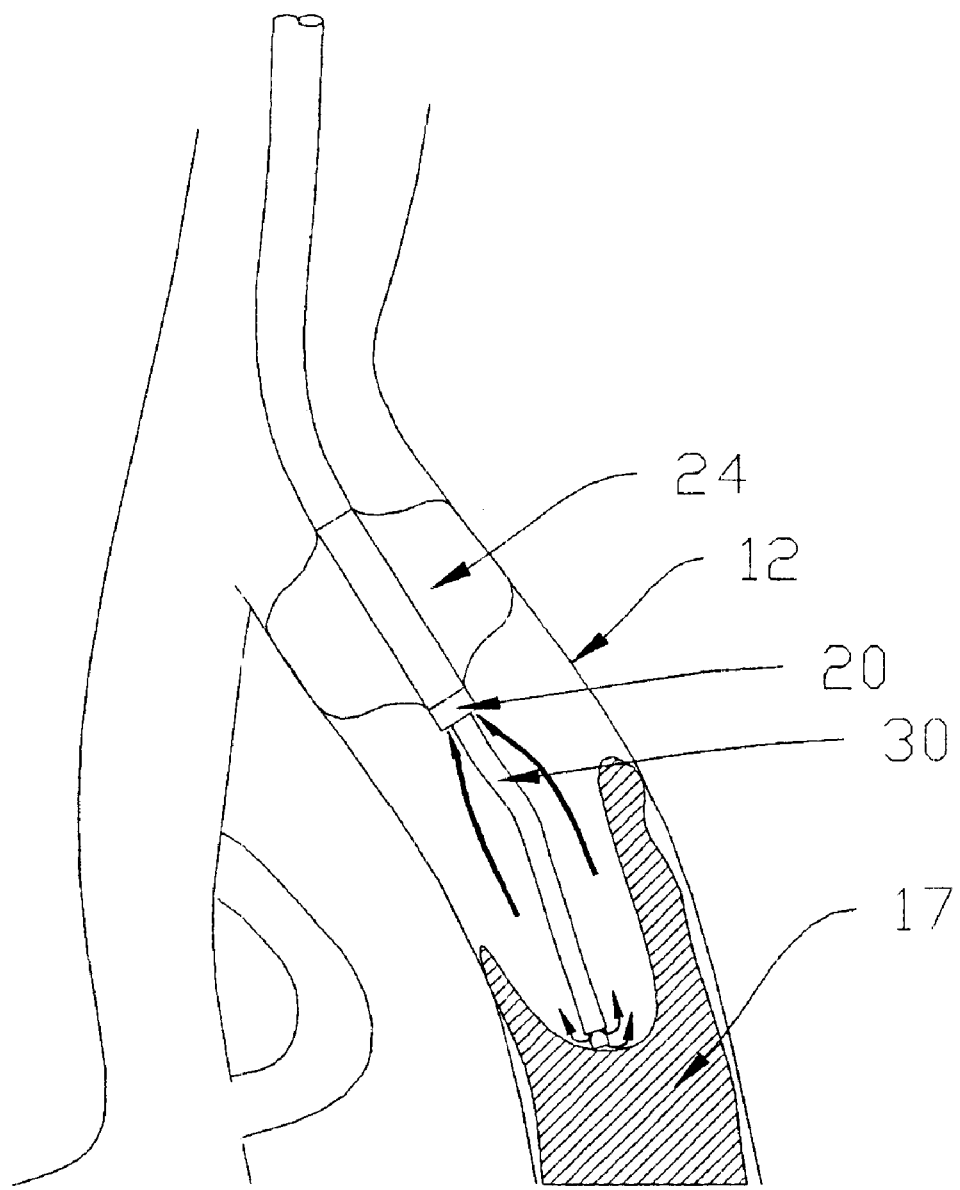

The above procedure is performed with the additional step of applying mechanical energy to the occlusion during flushing with the acidic dissolution solution. FIG. 9 shows mechanical energy being applied to the occlusion by contacting a guidewire 91 with the surface of the total occlusion during flushing. FIG. 10 shows mechanical energy being applied to the surface of the occlusion with the proximal end of the total occlusion insert. Other means of applying external energy, e.g. mechanical energy, may also be employed.

Example VIII

Coinfusion and Aspiration of Tissue Oxidant with a Reducing Deactivating Reagent A. Introduction Strong oxidizing agents capable of substantially dissolving organic constituents of tissues such as proteins, lipids, proteolipids, proteoglycans, and the like are infused through one lumen of a catheter device with a deactivating solution containing a readily oxidizable compound (compounds containing carbon, sulfur, etc) infused through another lumen of the same device. The mixed solution and dissolved or fragmented organics are then aspirated away from the treatment site through a larger third lumen. This chemical dissolution of tissue may be applied to areas of medicine such as in the removal of atherosclerotic plaque constituents, thrombus removal, or tumor removal.

B. Hypochlorite

The strong oxidant hypochlorite (HOCl) is used to partially dissolve and fragment purified type I collagen and a solution of sodium metabisulfite ($Na_2S_2O_5$) is used as the deactivating agent as the bisulfite ion is readily oxidized to sulfate ($SO_4^{(2-)}$). Activated carbon (C) may also be used as the deactivating reagent since it is a readily oxidizable carbon source which also scavenges excess chlorine from solution.

C. Hydrogen Peroxide

The strong oxidant hydrogen peroxide (30% in $H_2O$) is used to partially dissolve and fragment purified type I collagen and a solution of sodium metabisulfite ($Na_2S_2O_5$) is used as the deactivating agent as the bisulfite ion is readily oxidized to sulfate ($SO_4^{(2-)}$). Activated carbon (C) may also be used as the deactivating reagent since it is a readily oxidized carbon source.

Chemistry:

$Collagen + OCl^- \rightarrow CO_2 + H_2O + NH_2Cl + NH_3$ (protein oxidation, hypochlorite reduction)

$3OCl^- + S_2O_5^{(2-)} \rightarrow 2SO_4^{(2-)} + 3Cl^-$ (reduction of hypochlorite, oxidation of sulfur)

$2Cl_2 + C + 3H_2O \rightarrow 4HCl + CO_2 + H_2O$ (reduction of chlorine, carbon oxidation)

$2H_2O_2 + S_2O_5^{(2-)} \rightarrow 2SO_4^{(2-)} + H_2O + 2H^+$ (reduction of peroxide, oxidation of sulfur)

It is evident from the above discussion and results that improved methods of enhancing blood flow through a vascular occlusion are provided. Specifically, the subject invention provides a means for readily establishing fluid flow through a vascular site totally occluded by a calcified vascular occlusion, which has heretofore been difficult to practice. As such, the subject invention provides a means for using less traumatic procedures for treating peripheral vascular disease, thereby delaying or removing the need for graft procedures and/or amputation. A critical feature of the subject devices and methods is that only the target occlusion is subjected to the low pH conditions of the acidic dissolution solution. As such, unwanted contact of other portions of the target vascular site and/or host are avoided. This ability to employ concentrated dissolution fluids provides for a safe procedure that exhibits low toxicity. This ability to employ concentrated dissolution fluids also provides for a rapid procedure. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of enhancing fluid flow through a vascular site occupied by a vascular occlusion, said method comprising:

simultaneously flushing said vascular site with:
  (i) a dissolution fluid; and
  (ii) a dissolution fluid attenuating fluid;
for a period of time sufficient for fluid flow to be enhanced through said vascular site;
with the proviso that said simultaneous flushing occurs in a manner such that only a surface of said vascular occlusion is contacted with non-attenuated dissolution fluid and the remainder of said vascular site is not contacted with non-attenuated dissolution fluid;
whereby fluid flow is enhanced through said vascular site.

2. The method according to claim 1, wherein said vascular occlusion at least comprises organic matter.

3. The method according to claim 1, wherein said vascular occlusion at least comprises inorganic matter.

4. The method according to claim 1, wherein said vascular occlusion comprises both organic and inorganic matter.

5. The method according to claim 1, wherein said dissolution fluid is an organic matter dissolution fluid.

6. The method according to claim 5, wherein said organic matter dissolution fluid comprises an active agent selected from the group consisting of enzymes, surfactants, oxidizing agents and thrombolytic agents.

7. The method according to claim 1, wherein said dissolution fluid is an inorganic matter dissolution fluid.

8. The method according to claim 7, wherein said inorganic matter dissolution fluid is an acidic dissolution fluid.

9. The method according to claim 1, wherein said occlusion is a total occlusion.

10. The method according to claim 1, wherein said occlusion is a partial occlusion.

11. The method according to claim 1, wherein a catheter device is used to flush said surface of said vascular occlusion.

12. The method according to claim 11, wherein said catheter device comprises at least three different lumens.

13. The method according to claim 11, wherein said catheter device comprises at least four different lumens.

14. A system for use in enhancing fluid flow through a vascular site occupied by an vascular occlusion, said system comprising:
- a means for simultaneously flushing said vascular site with a dissolution fluid and a dissolution fluid attenuating fluid;
- a dissolution fluid; and
- an dissolution fluid attenuating fluid.

15. The system according to claim 14, wherein said means for simultaneously flushing said vascular site with a dissolution fluid and a dissolution attenuating fluid comprises two different fluid introducing means and a fluid aspiration means.

16. The system according to claim 14, wherein said flushing means is a catheter means.

17. The system according to claim 14, wherein said system further comprises:
(a) a manifold;
(b) a dissolution fluid reservoir;
(d) a dissolution fluid attenuating; and
(e) a source of negative pressure.

18. The system according to claim 14, wherein said system further includes a balloon inflation means.

19. The system according to claim 18, wherein said balloon inflation means is a syringe.

20. The system according to claim 14, wherein said system further comprises a guidewire.

21. A kit for use in enhancing fluid flow through a vascular site occupied by a vascular occlusion, said kit comprising:
- a means for flushing said vascular site with a dissolution fluid and a dissolution fluid attenuating fluid; and
- instructions for practicing the method of claim 1.

22. The kit according to claim 21, wherein said kit further comprises a dissolution fluid or a precursor(s) thereof.

23. The kit according to claim 21, wherein said kit further comprises a dissolution fluid attenuating fluid or precursors thereof.

24. The kit according to claim 21, wherein said kit further comprises a guidewire.

* * * * *